United States Patent [19]
Lenardo

[11] Patent Number: 6,083,503
[45] Date of Patent: Jul. 4, 2000

[54] INTERLEUKIN-2 STIMULATED T LYMPHOCYTE CELL DEATH FOR THE TREATMENT OF AUTOIMMUNE DISEASES, ALLERGIC RESPONSES, AND GRAFT REJECTION

[75] Inventor: Michael J. Lenardo, Potomac, Md.

[73] Assignee: The United States of America as represented by the Department of Health and Human Services, Washington, D.C.

[21] Appl. No.: 08/122,345

[22] Filed: Sep. 15, 1993

Related U.S. Application Data

[63] Continuation of application No. 07/751,090, Aug. 28, 1991, abandoned.

[51] Int. Cl.[7] ........................... A61K 39/00; A61K 45/05; A61K 31/66; A01N 57/00
[52] U.S. Cl. .................... 424/184.1; 424/85.1; 424/85.2; 514/903; 514/825; 514/885; 514/125; 436/506
[58] Field of Search ................................. 424/85.1, 85.2, 424/88, 89, 92; 514/903, 825, 885; 436/506

[56] References Cited

U.S. PATENT DOCUMENTS

| | | | |
|---|---|---|---|
| 4,469,677 | 9/1984 | Michael et al. ...................... | 424/276.1 |
| 4,904,481 | 2/1990 | Fathman . | |
| 5,260,422 | 11/1993 | Clark et al. ............................. | 530/403 |

OTHER PUBLICATIONS

BioWorld Today 8(77):1–4, see pp. 1 and 3 "AutoImmune Stock Sinks on Disappointing Phase III Myloral Trial Data in MS", Apr. 22, 1997.
Coates, A., et al., "Immune Protection Against Experimental Autoimmune Encephalomylelitis: Optimal Conditions and Analysis of Mechanism," *Cellular Immunology*, 12:370–381 (1974).
Alvord, E.C., Jr., et al., "Encephalitogen–Induced Inhibition of Experimental Allergic Encephalomyelitis: Prevention, Suppression and Therapy," *Annals N.Y. Acad. Sci.*, 122:333–345 (1965).
Rauch, H.C., "Short Communications: Modulation of Adoptive Cell Transfers in Experimental Allergic Encephalomyelitis by Antigen Treatment of Donors," *Cellular Immunology*, 60:220–227 (1981).
Raine, C.S., et al., "Suppression of Chronic Allergic Encephalomyelitis: Relevance to Multiple Sclerosis," *Science*, 201 (4354): 445–448 (1978).
Moller, G., "Do Suppressor T Cells Exist?", *Scand. J. Immunol.*, 27: 247–250 (1988).
Gonsette, R.E., et al., "Failure of Basic Protein Therapy for Multiple Sclerosis," *J. Neurol.*, 216:27–31 (1977).
Einstein, E.R., et al., "Protective Action of the Encephalitogen and Other Basic Proteins in Experimental Allergic Encephalomyelitis," *Immunochemistry*, 5:567–575 (1968).
Shaw, C., et al., "Suppression of Experimental 'Allergic' Encephalomyelitis in Guinea Pigs by Encephalitogenic Proteins Extracted from Homologous Brain," *J. Ex. Med.*, 160:171–180 (1960).

Eylar, E.H., et al., "Suppression of the Immune Response: Reversal of the Disease State with Antigen in Allergic Encephalomyelitis," *Nature*, 236:74–76 (Mar. 10, 1972).
Cunningham, V.R., et al., "Experimental Allergic Encephalomyelitis: Protection Experiments with Encephalitogenic Factor and Tubercle Fractions," *Annals N.Y. Acad. Sci.*, 122:346–355 (1965).
Lenardo, Michael J. (1991) "Interleukin–2 programs mouse $\alpha\beta$ T lymphocytes for apoptosis", *Nature*, 353:858–861.
Marx, Jean (1991) "Testing of Autoimmune Therapy Begins", *Science*, 252:27–28.
Sambhara, S., et al. (1991) "Programmed Cell Death of T Cells Signaled by the T Cell Receptor and the $\alpha_3$ Domain of Class I MHC", *Science*, 252:1424–1427.
Hemler, Martin E., et al. (1984) "Antigenic stimulation regulates the level of expression of interleukin 2 receptor on human T cells", *Proc. Natl. Acad. Sci.*, 81:2172–2175.
Lotze, Michael T., et al. (1985) "In Vivo Administration of Purified Human Interleukin 2", *The Journal of Immunology*, 135:2865–2875.
Roitt, Ivan M. (1988) *Essential Immunology*, Blackwell Scientific Publications, Oxford, 195–200.
Roitt, Ivan M., et al. (1985) *Immunology*, Gower Medical Publishing, London, p. 24.3.
Bitar, et al., *Cellular Immunology*, 112: 364–370 (1988).
Higgins, et al., *The Journal of Immunology*, vol. 140: 440–445, No. 2 (1988).
Nussenblatt, et al, *The Journal of Immunology*, vol. 144: 1689–1695, No. 5 (1990).
Waksman and Reynolds. Proc. Soc. Exp. Biol. Med 175:282–94 1984.
Russell et al. (1991) Proc. Natl. Acad. Sci. 88:2151–2155.
Liu et al. (1990) J. Exp. Med. 172:1735–1739.
Jones et al. (1990) Science 250:1726–1729.
Webb et al. (1990) Cell 63:1249–1256.

(List continued on next page.)

*Primary Examiner*—Nita Minnifield
*Attorney, Agent, or Firm*—Townsend and Townsend and Crew

[57] ABSTRACT

A method for the treatment or prevention of autoimmune diseases, allergic or atopic disorders, and graft rejection is provided, comprising inducing the death by apoptosis of a subpopulation of T lymphocytes that is capable of causing such diseases, while leaving substantially unaffected the majority of other T lymphocytes. Cell death is achieved by cycle(s) comprising challenging via immunization these T cells with antigenic substance at short time intervals, or by immunization followed by administering interleukin-2 (IL-2) when these T cells are expressing high levels of IL-2 receptor so as to cause these T cells to undergo apoptosis upon re-immunization with the antigenic peptide or protein. These methods are applicable to the treatment of autoimmune diseases such as, for example, multiple sclerosis, uveitis, arthritis, Type I insulin-dependent diabetes, Hashimoto's thyroiditis, Grave's thyroiditis, autoimmune myocarditis, etc., allergic disorders such as hay fever, extrinsic asthma, or insect bite and sting allergies, food and drug allergies, as well as for the treatment or prevention of graft rejection.

14 Claims, 6 Drawing Sheets

OTHER PUBLICATIONS

U.S. Pharmacopeial Convention Update (1992) 1:656.
Drug Interactions & Side Effects Index (1992) 46th Edition.
Ashwell et al. (1987) Journal of Exper. Medicine 165:173–194.
O'Brien et al. (1991) Seminars in Immunology 3:81–87.
Crabtree (1989) Science 243:355–361.
Paul (1989) *Fundamental Immunology*, 2nd Edition, Raven Press, NY pp. 804, 876–878, 898–902, 291–313, 10.
Kang et al. (1992) Science 257:1134–1138.
Allison (1991) Seminars in Immunology 3:73–74.
Havran et al. (1991) Seminars in Immunology 3:89–97.
Matzinger et al. (1989) Nature 338:74–76.
Sussman et al. (1988) Cell 52:85–95.
Rocha et al. (1991) Science 251:1225–1228.
Rellahan et al. (1990) Journal of Exper. Medicine 172:1091–1100.
Veterinary Pharmaceuticals & Biologicals (1990) Sixth Edition pp. 506, 543.
R. Patterson (1990) Allergic Diseases Diagnosis and Management JB Lippincott Co., Philadelphia, pp. 1–13, 17–21, & 52–57.
Cruse et al. (1992) in J. Cruse et al., ads., Clinical and Molecular Aspects of Autoimmune Disease, Karger, Basel, 1–17.
Lo, Research in Immunology, (1992), No. 3, vol. 143:296–299.
Kroemer et al., Research in Immunology (1992) No. 3 vol. 143:335–40.
Mercep et al., Science (1989) 246:1162–1165.
White et al. The VB Specific Superantigen Staphylococcal . . . Cell 56 pp. 27–35 1989.
Pelliard et al. Evidence for the Effects of a Superantigen in . . . Science pp. 325–329 Jul. 1991.
Ucker et al. Requirements for De Novo Transcription and Translation . . . J. of Immunol. 3461–69 1989.
Nau et al. Inhibition of IL–2 . . . J. of Immunol. 139:114–122 (1987).
Jansenn et al. T–cell Receptor/CDS Signaling . . . J. Immunol. 146:35–39 1991.
Wraith et al., (1989) Cell, 59:247–255.
Kawabe et al., (1991) *Letters to Nature*, 349:245–248.
McConkey et al. (1990) *Immunology Today*, 11(4):120–121.
Russell et al., (1991) *Proc. Natl. Acad. Sci. USA* 88:2151–2155.
M. Kronenberg (1991) *Cell*, 65:537–542.
Eylar et al. Neurochemical Research 4: 249–258, 1979.
Plotkin, S.A. et al. "Vaccines", published by U.B. Spunders Company, see p. 571, 1988.

No Antigen
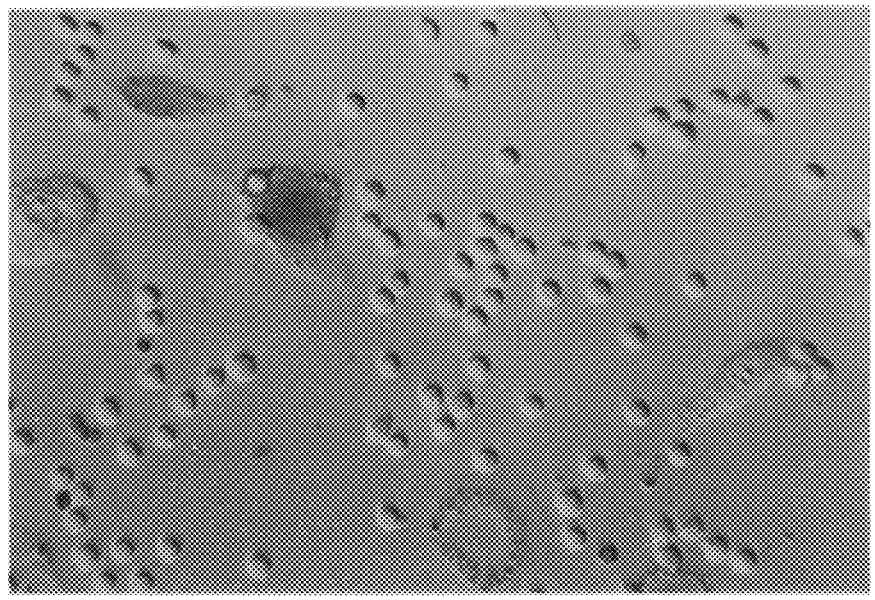
FIG. 1A₁
Untreated
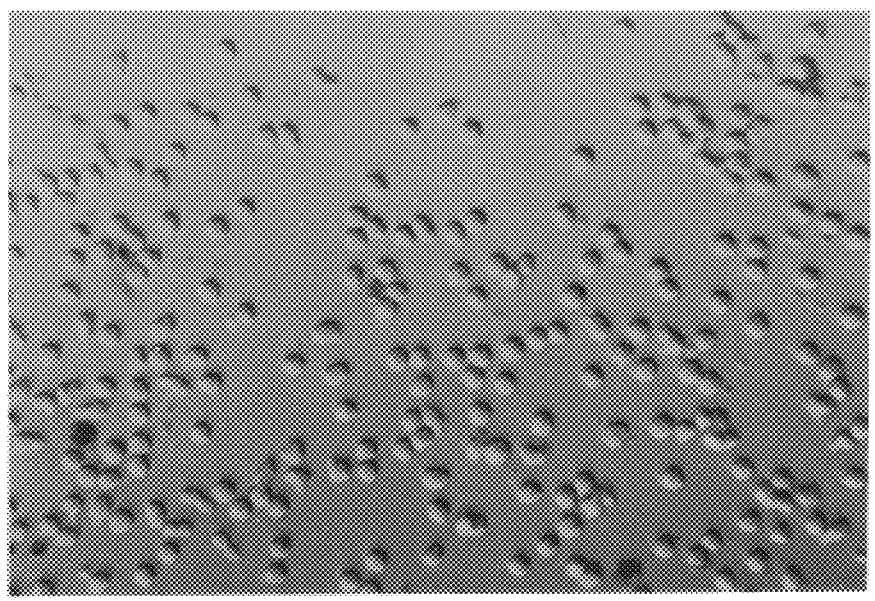
FIG. 1A₂

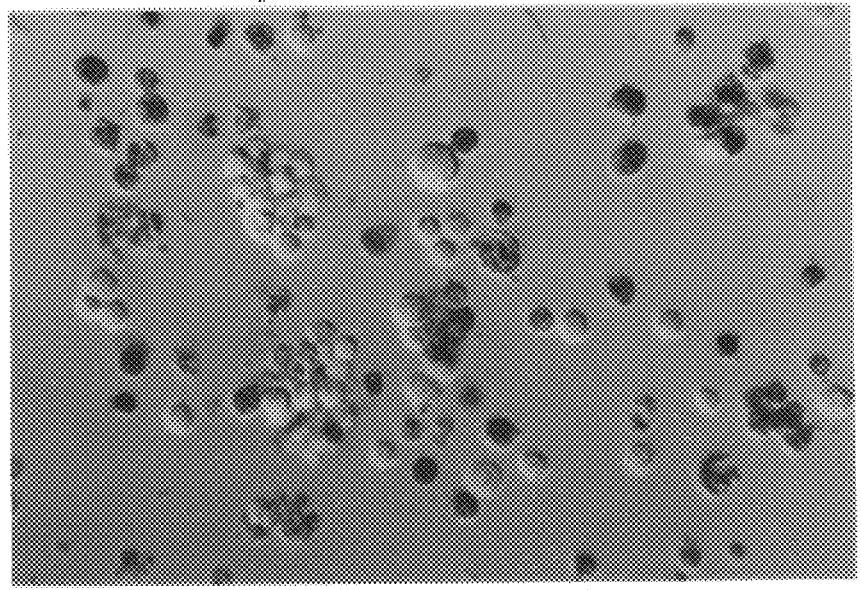
FIG. 1A₃
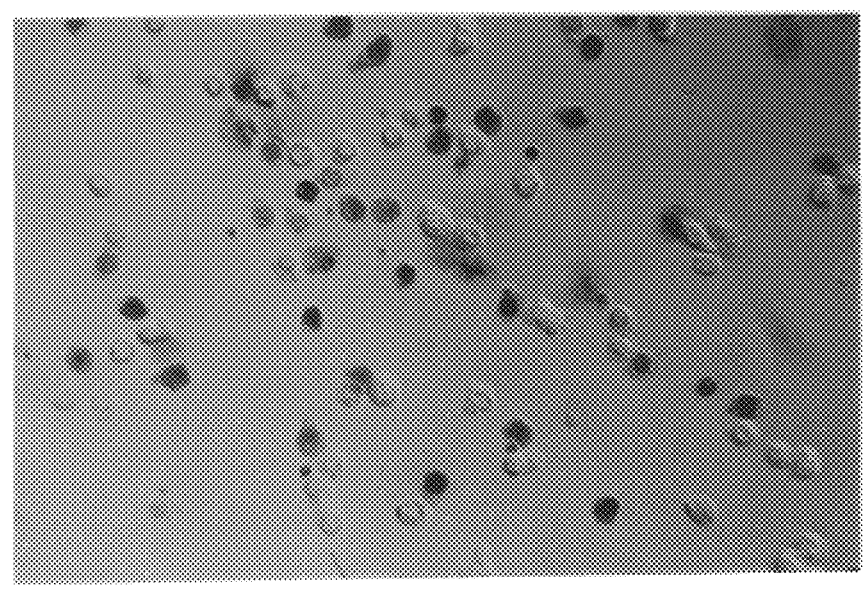
FIG. 1A₄

INTERLEUKIN-2 STIMULATED T LYMPHOCYTE CELL DEATH FOR THE TREATMENT OF AUTOIMMUNE DISEASES, ALLERGIC RESPONSES, AND GRAFT REJECTION

This is a continuation of application Ser. No. 07/751,090, filed Aug. 28, 1991, now abandoned.

BACKGROUND OF THE INVENTION

1. Field of the Invention

The present invention relates to the treatment and prevention of diseases that are primarily due to T cell immune responses. In particular, it relates to the suppression or elimination of certain autoimmune diseases, graft rejection, and allergic disorders by treatment with interleukin-2 (IL-2) and the specific antigen involved, thus allowing the killing of the subpopulation of T cells that recognizes this specific antigen. In this manner, IL-2 pretreatment sensitizes T cells to undergo programmed cell death following T cell receptor engagement.

2. Description of Related Art

Stimulation of the $\alpha\beta$ antigen receptor of mature T lymphocytes can lead to either proliferation or programmed cell death (1–4). Programmed cell death, termed apoptosis, is one mechanism for the clonal deletion of both thymocytes and mature T cells that establishes tolerance (5–9). A minor population (approximately 5%) of T lymphocytes of unknown function, termed $\gamma\delta$ cells, has been shown to undergo apoptosis following IL-2 treatment and antigenic stimulation (28). The role of apoptosis in the normal immune response, and the mechanism by which a mature T cell selects between proliferation and death, were not previously understood.

SUMMARY OF THE INVENTION

The present invention arose from the discovery that IL-2 programs mature T cells for antigen-driven death. The T cell death caused by IL-2 followed by antigen stimulation has hallmarks, such as DNA fragmentation and sensitivity to cyclosporin A, of "programmed cell death" or apoptosis. Thus, IL-2 acts as a death cytokine that will allow the demise only of T cells that are specifically stimulated through their antigen receptor. This novel use of a previously undiscovered property of IL-2 will allow the specific elimination of certain classes of antigen receptor-bearing T cells, forming the basis for new clinical applications of IL-2.

A critical determinant of the choice between T lymphocyte proliferation or programmed cell death is the prior exposure of these cells to interleukin-2 (IL-2). Antigen receptor stimulation in T cells not exposed to IL-2 causes normal activation, leading to IL-2 production and growth. In contrast, both $CD4^+$ and $CD8^+$ T cells previously exposed to IL-2 undergo apoptosis after antigen receptor stimulation. Therefore, antigen-activated T cells that are under the influence of IL-2 will respond to rechallenge by antigen by undergoing apoptosis. The timing is significant because later antigenic stimulation after the cells are no longer under the influence of IL-2 will cause growth rather than apoptosis. Antibody blockade of IL-2 but not IL-4 reverses the rapid and drastic reduction of lymph node $V\beta 8^+$ T cells caused in mice by the bacterial superantigen *Staphylococcus aureus* enterotoxin B. Thus, IL-2 may participate in a feedback regulatory mechanism by pre-disposing mature T lymphocytes to apoptosis.

At least three uses for this novel property of IL-2 can be envisioned.

First, there is an emerging set of findings that show that infusion of peptides derived from antigens involved in autoimmune diseases leads to the lessening of severity of such diseases (cf. 73). A variety of studies of the autoimmune disease experimental allergic encephalitis (EAE) shows that it is caused by the activation of T cells by immunization with myelin basic protein (MBP). Interestingly, infusion of peptides derived from the MBP sequence that stimulate the T cells that generate the disease are effective at blocking the disease (60). The discovery disclosed herein provides an explanation for these seemingly paradoxical observations, which is that the T cells are activated and stimulated by IL-2 during peptide infusion, and then undergo apoptosis when they are re-stimulated by the MBP antigen. Human diseases that have been associated with T cell activation by peptide antigens include multiple sclerosis and autoimmune uveitis (67; 69; 107). It is envisioned that these diseases, and, for example, systemic lupus erythematosus, systemic vasculitis, polymyositis-dermatomyositis, systemic sclerosis (scleroderma), Sjogren's Syndrome, ankylosing spondylitis and related spondyloarthropathies, rheumatic fever, hypersensitivity pneumonitis, allergic bronchopulmonary aspergillosis, inorganic dust pneumoconioses, sarcoidosis, autoimmune hemolytic anemia, immunological platelet disorders, cryopathies such as cryofibrinogenemia, autoimmune polyendocrinopathies, and myasthenia gravis can be approached by therapy which can now be modulated in a rationale way using IL-2 and the relevant peptide to cause apoptosis of the T cells responsible for the disease. The appropriate timing of IL-2 infusion or a repetitive immunization schedule could substantially augment the protective effect of the infused peptides.

Secondly, there is a significant body of literature that suggests that pre-immunization of an animal or man prior to engraftment with a foreign tissue prolongs the survival time of the graft (cf. 108). One example of this phenomenon is the "donor-transfusion effect," in which transfusing a patient about to receive an organ transplant with blood from the organ donor decreases rejection of the transplant. It is shown herein that CD8 cells are quite susceptible to IL-2-mediated apoptosis, and this is the primary class of T cells involved in graft rejection. Based on the discovery of this novel property of IL-2, $CD8^+$ T cells may be induced to undergo IL-2-mediated apoptosis; administering IL-2 during and immediately after the preimmunization/transfusion phase, or repetitive immunization with MHC antigen at appropriately short intervals, could augment T cell death, leading to greater tolerance of grafts.

Thirdly, a wide variety of atopic or allergic disorders, commonly known as asthma or allergies, results from the effects of activating T cells, which causes both the release of harmful lymphokines and the production of IgE by B cells (100,101). Over the past few decades, clinicians have made primitive attempts to treat these diseases by a "desensitization" process consisting of repetitive exposure to the same antigen that elicited the allergy (102). Despite the fact that very little is known about the mechanisms set in play by this procedure, in some cases such treatments were highly successful (102). An important scientific by-product of this work in clinical allergy is that considerable effort has gone into identifying proteins and other molecules that cause allergic responses (100). This has led to the identification of protein sequences for antigens such as Amb a V and Amb t V, which are ragweed allergens that cause hay fever, the protein sequence and characterization of antigenic peptides from allergen M that causes allergy to codfish (105), and the molecular cloning of the cDNA for antigen 5 of white-face hornet venom, associated with allergy to hornet stings (103). Drugs that can cause allergy are typically small organic molecules that may become immunogenic by forming covalent complexes with host proteins. In addition, a large variety of allergens have been prepared as protein extracts to be administered clinically to humans under the supervision of the Food and Drug Administration, and evaluated by a Panel on Review of Allergenic Extracts (102). With the molecular identification of these and other allergy-evoking antigens, it will be possible to immunize in cycle with IL-2 to induce apoptosis of T cells involved in allergic disorders such as allergic rhinitis, bronchial asthma, anaphylactic syndrome, urticaria, angioedema, atopic dermatitis, allergic contact dermatitis, erythema nodosum, erythema multiforme, Stevens-Johnson Syndrome, cutaneous necrotizing venulitis, and bullous skin diseases.

The key feature of each of these treatment protocols is that only the antigen-specific T cells which are a small component of the patient's T cell repertoire would be eliminated. The treatment would leave the patient's immune system largely intact. This is in contrast to present treatments that rely upon general immunosuppression that seriously incapacitates the host's immune function (see 109). Moreover, because this treatment causes death of the T lymphocytes, it is superior to other recently discovered mechanisms which do not kill T cells but rather cause functional inactivation or anergy which is typically reversible (98, 99). The experimental results described infra therefore have broad clinical significance in applications to human immunological diseases.

Throughout the history of immunological approaches to human and animal diseases, beginning with the first vaccination against smallpox carried out by Edward Jenner in 1798, the emphasis has been on stimulating a positive and protective antigen-specific immune response. In modern immunology, this is known to be due to activating lymphocytes. Hence, causing the activation and proliferation of antigen-specific immune cells, especially T lymphocytes, forms the basis of most of the clinical applications of immunology. In particular, the recent advent of molecularly cloned cytokines, especially those with the ability to cause the proliferation of immune cells, has furthered the clinical application of immunology. Such molecularly cloned cytokines can be readily prepared pharmacologically, and are powerful agents for stimulating the growth and division of lymphocytes. The conceptual and practical advance offered by the discovery disclosed herein is that cytokines such as IL-2, when given in sufficient quantity, also stimulate negative regulatory effects such as T cell apoptosis. These regulatory effects represent built-in mechanisms to limit or suppress the immune response. Thus, the recognition that these mechanisms exist, and the identification of a biologic, IL-2, that potently evokes antigen-specific T cell death, offers the opportunity to exploit the negative regulation of the immune response for the treatment of disease.

Accordingly, it is an object of the present invention to provide a method for treating or preventing a disease in a human or animal caused by antigen-activated T cells, comprising inducing the death by apoptosis of a subpopulation of T lymphocytes that is capable of causing said disease to an extent greater than that of other T lymphocytes. Said disease can include an autoimmune disease, graft rejection, or an allergic or atopic disorder, and said apoptosis can be achieved by exploiting endogenous IL-2, or by administering this substance exogenously. When IL-2 is administered exogenously, apoptosis can be achieved by a cycle comprising challenging via immunization said T cells with a substance selected from the group consisting of an antigen, a peptide, a protein, a polysaccharide, an organic molecule, and a nucleic acid, followed by administering a high dose of IL-2 when said T cells are expressing high levels of IL-2 receptor, so as to cause said T cells to undergo apoptosis upon reimmunization with said substance. When endogenous IL-2 is employed to achieve apoptosis, said cycle comprises challenging via immunization said T cells by repeated administration of said substance at intervals appropriate to cause apoptosis without the subsequent administration of a high dose of IL-2, relying instead on endogenous levels of IL-2.

Further scope of the applicability of the present invention will become apparent from the detailed description and drawings provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which.

DETAILED DESCRIPTION OF THE INVENTION

Figure 1B:
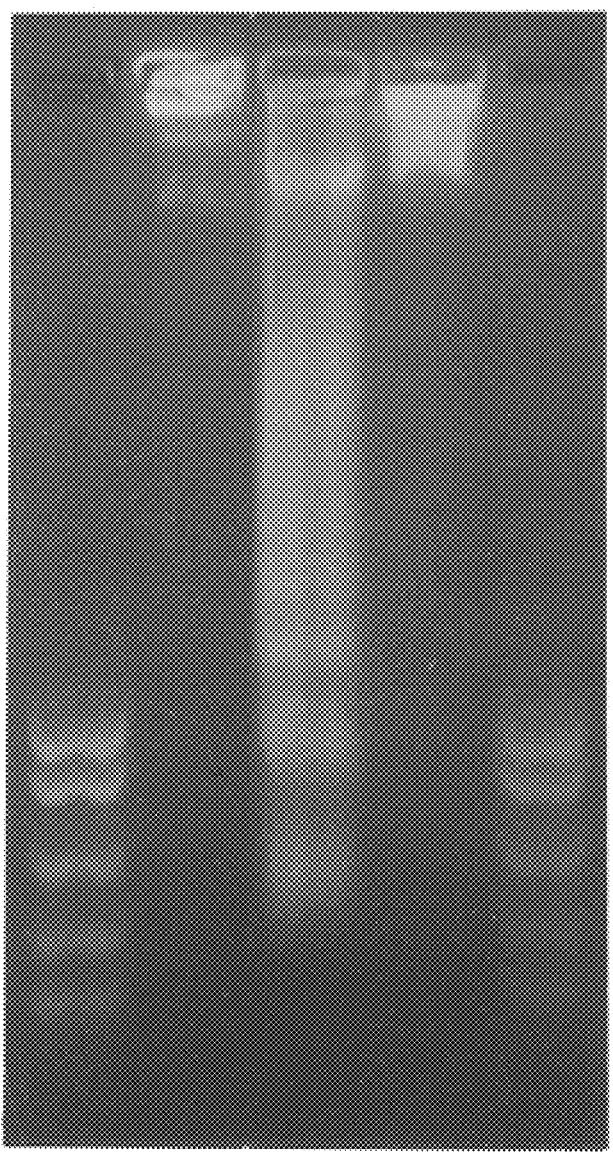
FIG. 1 shows apoptosis resulting from antigen or anti-CD$\epsilon$ stimulation of A.E7 T cells after IL-2 pre-treatment. (A) Photomicrographs of A.E7 T cells pre-treated with 100 units of IL-2, then stimulated and stained with trypan blue. (Top panels) Representative fields of A.E7 T cells (small round cells) and DCEK APCs (large fibroblastic cells) either with no antigen (left) or 1 $\mu$M pigeon cytochrome C peptide antigen (right). In addition to T cell death, antigen activation of A.E7 cells leads to the production of factors that cause lysis of DCEK APCs. (Bottom panels) Representative fields of A.E7 T cells in either untreated wells (lower left) or wells pre-coated with 10 $\mu$g/ml anti-CD3$\epsilon$ (lower right). Some non-adherent dead T cells and cell fragments, but not live cells, are washed away during the staining. Dark cells are cells that have died. (B) DNA prepared from equivalent numbers of A.E7 T cells was subjected to agarose gel electrophoresis and ethidium bromide staining. Lanes are from cells treated as in (A) with IL-2 and/or anti-CD$\epsilon$ (145-2C11) as indicated. End lanes (M) contain pBR322/ Msp I DNA markers.

The disclosures of each of the references cited in the present application are herein incorporated by reference in their entirety.

The following detailed description of the invention is provided to aid those skilled in the art in practicing the same. Even so, the following detailed description should not be construed to unduly limit the present invention, as modifications and variations in the embodiments herein discussed may be made by those of ordinary skill in the art without departing from the spirit or scope of the present inventive discovery.

The effect of IL-2 on antigen response was first observed in A.E7, a non-transformed CD4$^+$ T$_H$1 T lymphocyte clone that constitutively expresses high-affinity IL-2 receptor and produces IL-2 after antigen stimulation (10,11). Resting A.E7 cells given 1 μM antigen underwent proliferation due to endogenous IL-2 production (from 435 to 22894 CPM [$^3$H]thymidine). By contrast, A.E7 cells given 100 units/ml exogenous IL-2 for two days and then 1 μM antigen showed decreased [$^3$H]thymidine incorporation (51755 to 7140 CPM). Decreased incorporation might have been due to an antigen-dependent block in IL-2 stimulated proliferation (12,13), but microscopic examination unexpectedly revealed extensive death of the T cells (FIG. 1A, upper panels). For the IL-2 pre-treated sample, quantitation revealed 82% fewer T cells following 1 μM antigen stimulation compared to control (Table 1). Cell death was less dramatic with lower doses of IL-2, but was still evident between 2 and 5 units/ml, at which 50–60% of the T cells were killed (Table 1). A smaller cell loss was seen in T cells given no IL-2 pre-treatment that could be attributed to IL-2 produced by antigen stimulation. These results suggested the hypothesis that IL-2 following antigen stimulation leads to proliferation, whereas IL-2 exposure prior to antigen stimulation causes cell death.

TABLE 1

Effect of IL-2 and antigen receptor stimulation on T cell viability

| Cells | Pretreatment | Cell Number/well (× 10$^{-4}$) | | stimulated % control |
|---|---|---|---|---|
| A.E7 | Expt 1 | Control | 1 μM antigen | |
| | no IL2 | 3.8 ± 0.3 | 2.3 ± 1.8 | 60% |
| | 100 units IL2 | 4.9 ± 2.5 | 0.9 ± 0.6 | 18% |
| | Expt 2 | | | |
| | no IL2 | 3.6 ± 0.4 | 2.8 ± 0.6 | 78% |
| | 2 units IL2 | 5.0 ± 0.4 | 2.4 ± 0.1 | 48% |
| | 5 units IL2 | 6.2 ± 0.5 | 2.4 ± 0.4 | 39% |
| | 10 units IL2 | 6.8 ± 0.6 | 2.0 ± 0.2 | 29% |
| | 50 units IL2 | 6.8 ± 1.0 | 2.0 ± 0.7 | 29% |
| | Expt 3 | Control | 10 μg/ml anti-CD3ε | |
| | no IL2 | 4.3 ± 0.5 | 3.2 ± 0.4 | 74% |
| | 2 units IL2 | 7.1 ± 1.5 | 3.6 ± 0.1 | 51% |
| | 5 units IL2 | 6.4 ± 0.8 | 2.1 ± 0.6 | 33% |
| | 10 units IL2 | 7.4 ± 1.5 | 1.0 ± 0.2 | 14% |
| | Expt 4 | Anti-CD3ε | Anti-CD3ε + CsA | |
| | no IL2 | 3.9 ± 0.5 | 4.4 ± 0.5 | — |
| | 25 units IL2 | 2.2 ± 0.5 | 4.2 ± 0.9 | — |
| | | Control | 20 μg/ml anti-Vβ8 | |
| LNT | 3 units IL2 | 5.7 ± 1.1 | 9.1 ± 1.2 | 160% |
| | 100 units IL2 | 39.8 ± 2.0 | 20.1 ± 6.4 | 50% |
| | | 33 μg/ml anti-Vβ6 | | |
| | 3 units IL2 | | 9.4 ± 1.0 | 165% |
| | 100 units IL2 | | 26.8 ± 4.7 | 67% |

Cell counts (×10$^{-4}$) are averages of 4–6 independent hemocytometer counts of three wells determining only trypan-blue excluding cells. Antigen was the 81–104 peptide from pigeon cytochrome c (a gift of B. Beverly). The anti-CD3ε antibody 145-2C11 (16) was used at the concentrations indicated, except for Expt. 4 where 2.5 μg/ml was used. Plates were coated with 20 μg/ml anti-Vβ8 (F23.1 MAb) and 33 μg/ml anti-Vβ6 MAb(RR4-7MAb) as described in the legend to FIG. 1. Control experiments in which equivalent amounts of MAb recognizing CD4, MHC class I, or CD45 were coated on plates had no effect on cell viability (data not shown). Cells were incubated in dishes for 48 hours. Trypan blue stained cells (blue) made up 30–70% of the differences between stimulated and controls where quantitated. Cyclosporin A (CsA, a gift from Sandoz Pharmaceuticals, Inc.) was included at 100 ng/ml only during the stimulation by 145-2C11 antibody. IL-2 was human recombinant IL-2 (provided by Dr. Craig Reynolds, Biological Response Modifiers Program, NCI) or supernatant from MLA-144 cells (provided by the Fermentation Laboratory, FCRF, NCI), both of which gave essentially identical results. Data are representative of 8 experiments.

To test this idea, IL-2 and antigen stimulation were evaluated in an experiment in which endogenous IL-2 was not produced. A.E7 cells (and other CD4$^+$ T$_H$1 T cell clones) require a co-stimulatory signal from antigen-presenting cells (APCs) in addition to occupancy of the T cell receptor complex to produce IL-2 (14,15). Therefore, in the absence of APCs, A.E7 cells were pre-treated with IL-2, washed, and stimulated on culture dishes coated with a monoclonal antibody (MAb) to CD3ε complex (16). This resulted in almost no endogenous IL-2 production (data not shown). Nonetheless, IL-2 pre-treatment followed by anti-CD3ε stimulation again led to extensive T cell death (FIG. 1A, lower panels). Quantitation showed that 74% of the untreated cells, but only 14% of the T cells pre-treated with 10 units/ml of IL-2, were recovered alive (Table 1). As was observed with antigen stimulation, killing caused by anti-CD3ε was dependent on the IL-2 dose, with 49% cell loss at 2 units/ml. Dying A.E7 cells exhibited a pattern of DNA fragmentation to 200 bp nucleosome-length multiples after IL-2 and anti-CD3ε stimulation (FIG. 1B, 2C11). Also, cell death was abrogated by cyclosporin A (Table 1, CsA). Together, these data strongly suggested that apoptosis was occurring (1,2,5,7).

It was then tested whether IL-2 could predispose cells bearing particular T-cell receptors (and not bystander cells) to apoptosis in a heterogeneous lymph node T (LNT) cell population. Because LNT cells do not constitutively express IL-2 receptors, they were first stimulated with the lectin concanavalin A. This caused the cells to express the IL-2 receptors and become IL-2-responsive (data not shown). The concanavalin A was then removed and the cells were exposed to IL-2. Since LNT cells did not survive without any IL-2, low dose (3 units/ml) and high dose (100 units/ml)

IL-2 were compared. IL-2 was given for two days and the LNT cells (>97% αβ T cells, data not shown) were plated on dishes coated with either no antibody, the F23.1 monoclonal antibody (MAb)(anti-Vβ8, specific for the Vβ8.1,2,3 receptor chains) (17), or the RR4-7 MAb (anti-Vβ6) (18). In low IL-2, both anti-Vβ8 and anti-Vβ6 MAbs caused the cell number to increase (Table 1). After high IL-2, anti-Vβ8 caused nearly 50% cell loss, and anti-Vβ6 led to a 33% cell loss (Table 1). Flow cytometry revealed that anti-Vβ8 MAb markedly deleted cells with cognate Vβ8 receptors in LNT cells given high IL-2 but not in LNT cells given low IL-2 (data not shown). To accurately quantitate the deletion observed with high dose IL-2, the populations were gated separately into CD4$^+$ cells and CD4$^-$ cells (virtually all CD8$^+$ cells, see legend) (Table 2). Anti-Vβ8 MAb decreased the fraction of Vβ8$^+$ cells from 38.4% to 14.1% for CD4$^+$ cells and from 38.0% to 19.4% for CD4$^-$ (CD8) cells but had no effect on Vβ6$^+$ cells, which were relatively increased to compensate for the loss of Vβ8$^+$ cells (Table 2). Similarly, anti-Vβ6 MAb caused deletion of Vβ6$^+$ cells (from 12.3% to 1% for CD4$^+$ cells and from 10.0% to 2.2% for CD4$^-$ (CD8) cells), but not Vβ8$^+$ cells, which were relatively increased (Table 2). These findings were not due to T cell receptor down-modulation because: 1) substantial apoptosis and decreased cell number were observed; 2) cells bearing heterologous receptors were relatively increased; and 3) no T cell receptor negative cells were detected (data not shown). Thus, IL-2 pre-disposes to an endogenous death pathway in both CD4$^+$ and CD8$^+$ T cells. Bystander cells, though competent to undergo apoptosis, are not affected by antigen-receptor-mediated killing of a subpopulation of LNT cells.

TABLE 2

Flow cytometric quantitation of in vitro deletion of Vβ8- and Vβ6-bearing LNT cells using anti-receptor antibodies

| Gating | Fraction of total gated cells positive for: | Stimulation after IL-2 pre-treatment | | |
|---|---|---|---|---|
| | | None | Anti-Vβ8 | Anti-Vβ6 |
| CD4+ cells | Vβ8 | 38.4% | 14.1% | .3% |
| | Vβ6 | 12.3% | 15.9% | 1.0% |
| CD4− (CD8) cells | Vβ8 | 38.0% | 19.4% | 40.6% |
| | Vβ6 | 10.0% | 16.4% | 2.2% |

Figure 2:
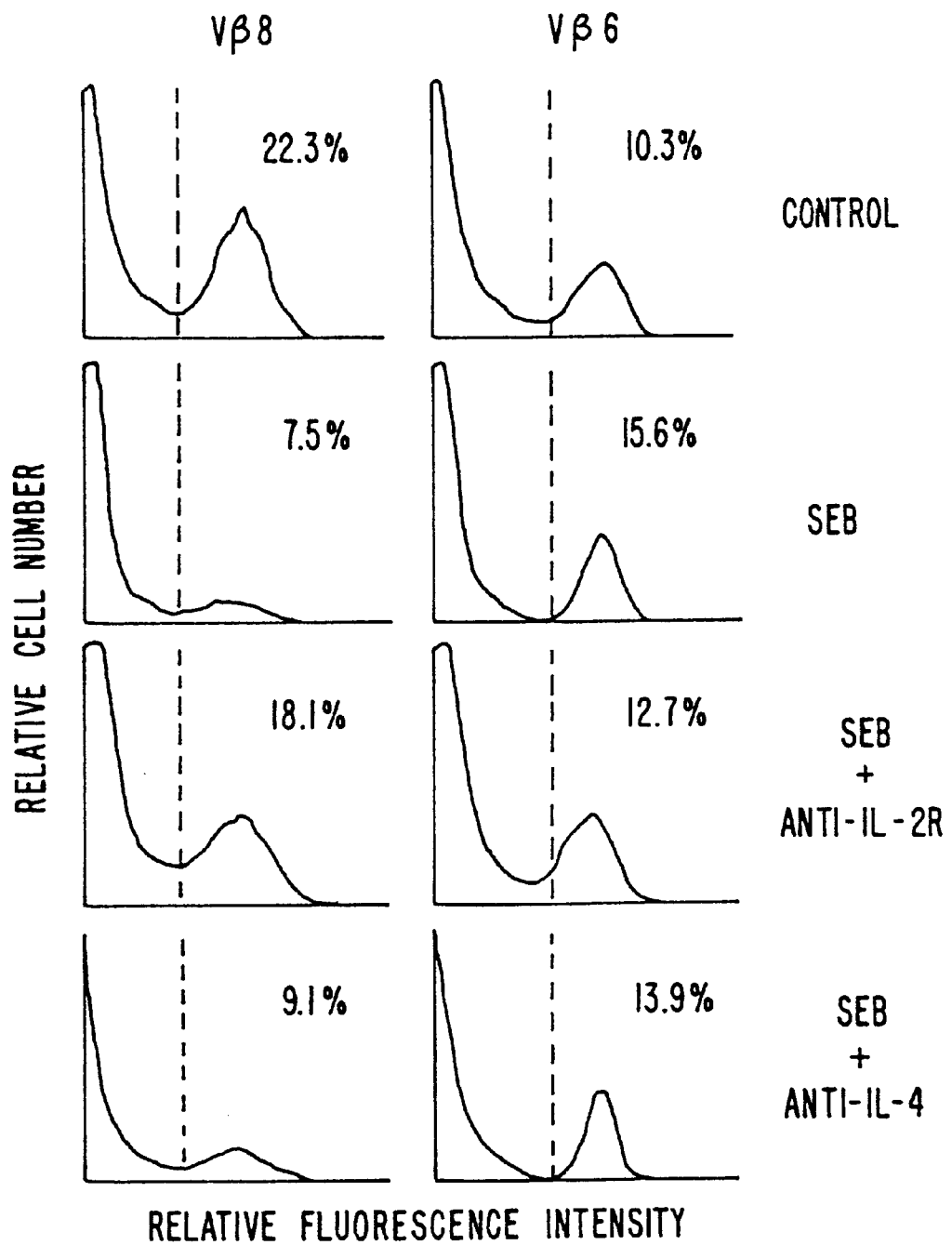
FIG. 2. shows IL-2 dependent clonal elimination of V$\epsilon$8 T cells by immunization with SEB. Histograms of flow cytometry analysis of lymph node T cells taken from mice that were either uninjected (Control), injected with SEB (SEB), injected with SEB and the MAb 3C7 that blocks the binding of IL-2 to the IL-2 receptor $\alpha$ chain (SEB+anti-IL-2R), or injected with SEB and the MAb 11B11 that blocks IL-4 (SEB+anti-IL-4).

Lymph node T cells pre-treated with 100 units/ml IL2 were prepared as described in FIG. 2 and stimulated on culture dishes coated with either no antibody or MAb against either Vβ8 (F23.1) or Vβ6(RR4-7). Cells recovered from the plates were stained for two color cytometry with both anti-CD4 (Becton Dickinson) and either anti-Vβ8 (F23.1) or anti-Vβ6 (RR4-7). The CD4 staining was used to gate the cells into CD4$^+$ and CD4$^-$ pools; control staining showed that virtually all CD4$^-$ cells were CD8$^+$ (using anti-Lyt2), and cells were >97% αβ T cells (using H57-597) in these preparations. The gated pools were then quantitated by flow cytometry using a Becton Dickinson FACSCAN for the fraction of either Vβ8$^+$ or Vβ6$^+$ cells. Independent gating was necessary for accurate quantitation because of the previously described overgrowth of CD8 cells in antibody stimulated samples (29). The fraction of the gated pool that was positive for either Vβ8 or Vβ6 is given as percent; boxed values show conditions where deletion was observed. The data are representative of 5 experiments.

The hypothesis that IL-2 preceding antigen receptor occupancy leads to apoptosis predicted that repetitive immunization could eliminate antigen-specific T cell clones in vivo. Furthermore, such elimination would depend on IL-2 produced by activated T cells predisposing themselves and their progeny to death. To test this prediction, BALB/c mice were given *Staphylococcus aureus* enterotoxin B (SEB) I.V. using a loading dose of 500 μg followed by two injections of 125 μg at two day intervals. SEB was used because it activates all T cells bearing a Vβ8 polypeptide chain in their T cell receptor. Vβ8-bearing cells comprise nearly one quarter of the repertoire of a BALB/C mouse, and therefore can be measured easily by flow cytometry. After eight days, the mice were sacrificed, and peripheral lymph node T cells were analyzed for Vβ8$^+$ cells (which are specifically activated by SEB) and Vβ6$^+$ cells (which are not stimulated by SEB) (19). Flow cytometry for representative mice is shown in FIG. 2. In an uninjected animal, 22.3% of the T cells were detected by the antibody KJ16-33 (20) which recognizes Vβ8.1,8.2 receptors. As predicted, repetitive immunization with SEB reduced the relative number of Vβ8.1,8.2$^+$ cells to 7.5%, over a 60% decrease. Injection of SEB together with 800 μg of MAb 3C7, an IL-2 receptor alpha chain blocking antibody (21,22), (anti-IL-2R, a gift of Dr. A. Kruisbeek) every 12 hours I.P. caused a striking reversal of the loss of Vβ8.1,8.2$^+$ cells to 18.1%. Co-injection of MAb 11B11 previously used to block IL-4 responses in vivo (22,23) (anti-IL-4, a gift of Dr. W. Paul), did not reverse the loss of Vβ8.1,8.2$^+$ cells caused by SEB (Table 2). The fractions (mean ±S.D.) of Vβ8.1,8.2$^+$ cells for several mice were similar: normal, 23.3±0.6% (n=4), SEB only, 9.7±2.8% (n=4), SEB+anti-IL-2R, 19.5±3.8% (n=3), and SEB+anti-IL-4, 9.4±1.8% (n=3). Vβ6$^+$ T cells showed no deletion in these mice. A similar blocking effect was observed using the MAb S4B6 that directly binds the IL-2 lymphokine molecule itself (data not shown). No effects on the number of Vβ8 or Vβ6 cells were seen if antibody 3C7 or 11B11 was injected without SEB (data now shown). Moreover, no evidence of Vβ8 T cell redistribution from lymph into other tissues was found by pathological analysis (data not shown). Thus, clonal elimination caused by SEB under these conditions depends on IL-2 but not IL-4.

By three different experimental protocols, a direct involvement of IL-2 in antigen-receptor driven T lymphocyte elimination was found. IL-2-induced apoptosis has the features of feedback inhibition (25): i) it is caused by an "end-product", e.g., IL-2, of the initial antigen stimulation; ii) apoptosis was greater with increasing doses of IL-2; and iii) it reverses the increased T cell numbers initially caused by antigen (1,4,8,9). T cell clonal specificity is maintained by the requirement for antigen stimulation as well as IL-2 for apoptosis; however, antigen receptor occupancy alone is not sufficient for apoptosis. A useful term for this feedback pathway would be "propriocidal" regulation (Latin: proprius, "one's own") to indicate selective killing of the stimulated T cells, their progeny, and clones of related specificity. One conceivable role of this pathway may be illustrated by Staphylococcal enterotoxins whose lethality seems due to substances produced by activated T cells (19,26). IL-2-mediated apoptosis could eliminate the affected T cells and decrease the harmful effects of chronic exposure to these toxins.

These results have been extended to human T lymphocytes (74). Human peripheral blood T lymphocytes were stimulated to express the high affinity IL-2 receptor using either phytohemagglutinin or concanavalin A. These cells were then stimulated with either 0, 2, or 200 units of IL-2.

Figure 3:
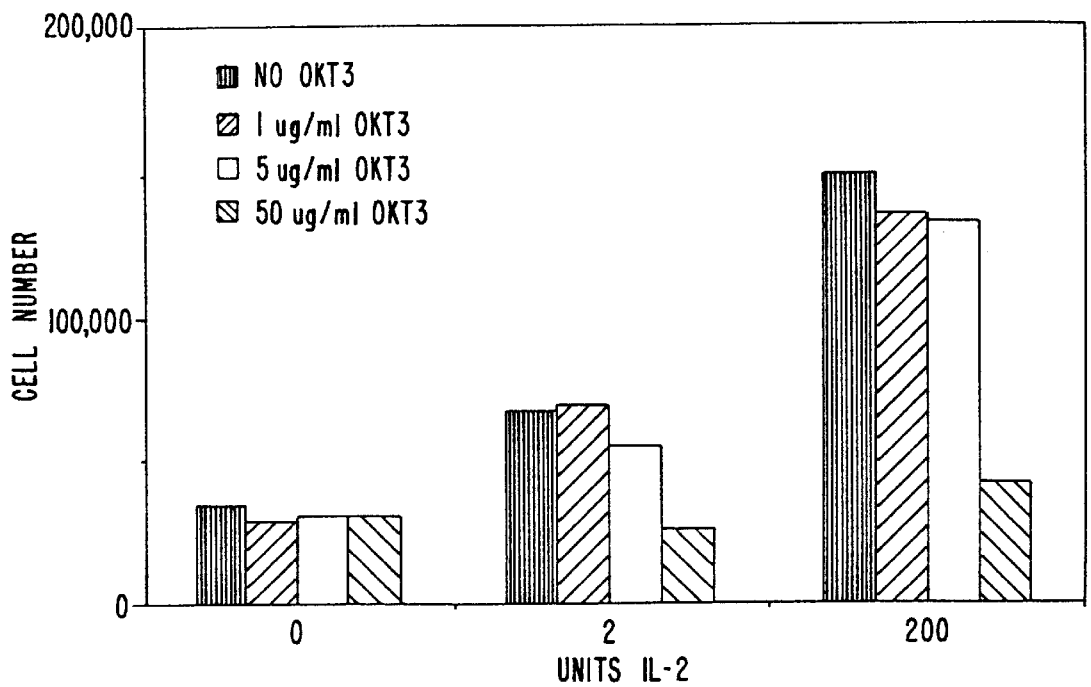
FIG. 3 shows the decrease in human T cell number when given IL-2 followed by stimulation through the T cell receptor CD3 polypeptide using the monoclonal antibody OKT3.

Proliferation and an increased cell number were observed in response to IL-2 (FIG. 3). Upon rechallenge of the cells with an antigen surrogate, namely, a MAb against a human CD3 polypeptide of the T cell receptor (OKT3), the cell numbers dropped if the cells had previously been exposed to IL-2 but not if they were untreated (FIG. 3). In samples pretreated with IL-2 and then re-stimulated with OKT3, ladders of fragmented DNA were also observed by agarose gel electrophoresis, indicating that apoptosis was occurring (data not shown). Thus, the ability of IL-2 to predispose to apoptosis is not a peculiarity of murine T cells, but also extends to human T lymphocytes, and most likely represents an intrinsic T cell regulatory mechanism. This therefore makes it possible to exploit antigen-driven T cell apoptosis for the treatment of diseases in humans, mice, and presumably mammals or other animals that have T cells with similar properties.

FIG. 1: The A.E7 T cell is a non-transformed $CD4^+$ $T_H1$ T cell clone that produces IL-2 after stimulation by a pigeon cytochrome C peptide (amino acids 81–104) in the context of $E^k$ that was carried as described previously (11,14). Lympholyte-M purified A.E7 T cells were pre-treated for 48 hours with MLA-144 gibbon ape leukemia cell supernatant to provide 100 units/ml of IL-2 activity. T cells were harvested, washed 3 times with medium (Click's medium with 10% fetal calf serum, 2 mM glutamine, and 50 $\mu$M β-mercaptoethanol added; Biofluids, Inc.) and stimulated in 96-well dishes. Antigen stimulations contained $2\times10^4$ T cells, $1\times10^4$ DCEK ($E_\alpha$, $B_\beta{}^K$—expressing L cell transfectants, a gift of Dr. Ronald Germain, NIH) APCs given 3000 Rads, and 1 $\mu$M purified pigeon cytochrome C peptide (amino acids 81–104) in 200 $\mu$L total volume. For thymidine uptake, after 24 hours, 0.5 $\mu$Ci of [$^3$H]TdR (Amersham) was added, incubation was continued for 8 hours, and samples were then assayed by scintillation counting. For photomicroscopy, after 40 hours of stimulation, the medium was replaced with 0.4% trypan blue in phosphate buffered saline (PBS, 0.8 mM potassium phosphate, 154 mM sodium chloride, and 2.9 mM sodium phosphate, pH 7.4) for 10 minutes. The stain was removed and the wells gently washed three times with PBS only. Photomicrographs were made on a Zeiss Axiovert 405 M microscope using Hoffman modulation contrast optics. Antibody stimulations used 96-well plastic culture dishes coated with 10 $\mu$g/ml solutions of protein A column-purified anti-CDeMAb (145-2C11) (15) in PBS for 4 hours at 37° C. Wells were washed two times with PBS, once with medium, and filled with $5\times10^4$ A.E7 T cells in 200 $\mu$L of medium. Lymph node T cells (for Tables 1 and 2) from axillary, inguinal, and mesenteric nodes excised from BALB/c mice were placed into medium containing 3 $\mu$g/ml concanavalin A for 48 hours, then treated with 10 mg/ml α-methylmannoside for 30 minutes, washed extensively, and placed in culture for 48 hours with either 3 or 100 units of IL-2. Antibody stimulations (F23.1 and RR4-7) were in 75 cm$^2$ culture flasks coated with antibodies as in FIG. 2 and inoculated with $1\times10^7$ cells in 12 mls medium containing either 5 or 100 units IL-2/ml. Cells were harvested, isolated by Lympholyte-M, and stained for cytometry. DNA preparations of A.E7 cells stimulated with IL-2 and anti-CD3ε (scaled to 5 mls) were carried out as described previously (5).

FIG. 2: Vβ8 samples (left panels) were stained with MAb KJ16-133 (20) which detects Vβ8.1,8.2 TCRs and Vβ6 samples (right panels) were stained with MAb RR4-7[18] for Vβ6 TCRs. Histograms are relative fluorescent intensity versus cell number; positive cells, as gated by the dotted line, are percentages of total T cells. Female, six-week-old BALB/c mice were injected with Staphyloccocal enterotoxin B (Sigma) diluted in 250 $\mu$L sterile 1× PBS in the tail vein as follows: day 0–500 $\mu$g, day 2–125 $\mu$g, and day 4–125 $\mu$g. Lymph node T cells did not express IL-2 receptor a chain until 12 hours after the first SEB injection; therefore, I.P. injections of 800 $\mu$g of MAb 3C7 were initiated 12 hours after the first SEB dose, and given every 12 hours until the experiment ended. MAb 3C7 has been shown to block IL-2 responses, and this preparation blocked IL-2 responses in vitro (ref. 21, 22 and M.J.L., unpublished results). MAb 11B11 was given similarly in 1 mg doses. Each MAb injection was given in 300 $\mu$L of 5% dextrose in water, which provided a simple metabolite and hydration to prevent mortality of the mice during the course of each experiment. After eight days, the mice were sacrificed, and lymph node cells were directly stained. Staining for flow cytometry was carried out in 1× PBS with 0.1% bovine serum albumin and 0.1% sodium azide with pre-determined dilutions of primary antibody (mouse immunoglobulin (Ig) γ2a MAb F23.1 or rat IgG2b, KJ16-133 for Vβ8 or rat IgG2b RR4-7 for Vβ6) followed by either a fluorescein isothiocyanate-conjugated goat anti-mouse IgG2a (Southern Biotechnology) or a goat F(ab')$_2$ anti-rat IgG H and L (Caltag Laboratories). CD4 was detected with phycoerythrin-conjugated anti-L3T4 antibody (Becton-Dickinson). Minor residual dead cells were gated by propidium iodide. Samples were 50,000 events analyzed with 3 decade logarithmic amplification on a Becton-Dickinson FACS 440 dual laser cytometer interfaced to a Digital Equipment Corporation PDP 11/24 computer and plotted as isocontours of total cell number.

FIG. 3: Human peripheral blood mononuclear cells were purified by Ficoll density gradient centrifugation from blood packs obtained from anonymous donors through the Department of Transfusion Medicine at the National Institutes of Health. The cells were incubated in RPMI 1640 medium with 10% fetal calf serum, and aliquots of cells were given 5 $\mu$g/ml concanavalin A for 2–3 days. Cells were then harvested, quantitated, and incubated in flat-bottom plastic dishes pre-coated with either 0, 1, 5 or 50 $\mu$g/ml OKT3 MAb. After 2–3 days, 4–6 cell counts were performed and averaged for each point.

The findings described above establish a direct role for IL-2 in clonal elimination of mature T cells, which is postulated to be a mechanism of extra-thymic tolerance (1,4,8,9). Recently, Kawabe and Ochi have shown that the loss of mature Vβ8 cells following SEB injection is the result of apoptosis (1). This study demonstrates that loss of Vβ8$^+$ T cells may be faster and greater in magnitude if larger amounts of SEB are repeatedly administered. This would support the model that antigen re-stimulation of T cells under the influence of IL-2 will cause apoptosis.

How does IL-2, which is well known for its mitogenic effect on T lymphocytes, paradoxically program the same cell-type for apoptosis? One possibility is that IL-2 serves only to drive T cells into the division cycle, which has been recently suggested to pre-dispose thymocytes and γδ T cells to death (27,28). If this is true, then any successful immune response could pre-dispose mature αβ T cells to apoptosis. Alternatively, IL-2 could provide a qualitatively or quantitatively distinct signal that entrains apoptosis to antigen receptor stimulation. In either case, in evaluating IL-2 as a therapeutic agent in humans, it will be important to consider its unexpected ability to pre-dispose T cells to apoptosis.

Therapeutic Applications in Human and Veterinary Medicine

I. General Principles.

The discovery that interleukin-2 (IL-2) predisposes T lymphocytes to programmed cell death, or apoptosis, allows for a novel method of therapeutic intervention in disease processes in humans and animals primarily caused by the action of T cells (30). In essence, this involves specifically inducing the death of a subpopulation of T lymphocytes that are capable of causing disease, while leaving the majority of T lymphocytes substantially unaffected. This method of intervention contrasts with, and is potentially far superior to, currently used therapeutic methods that cause a general suppression or death of T lymphocytes. Examples of widely-used general immunosuppressive agents are corticosteroids, such as prednisone, which are used to treat autoimmune diseases and allergic conditions, and cyclosporin A, which is used for treating graft rejection (31). These treatments suffer from the drawback of severely compromising immune defenses, leaving the patient vulnerable to infectious diseases. The two key elements of the present process are that: i) only the subset of T cells that reacts with antigens that cause the disease are affected by the treatment; and ii) the T cells affected by the treatment are killed, i.e., they are permanently removed from the repertoire.

Several general principles underlie the present process. T cells recognize antigen in the form of short peptides that form noncovalent complexes with major histocompatibility complex (MHC) proteins on the surface of antigen-presenting cells found throughout the body (32). Antigens may also take the form of polysaccharides, organic molecules, or nucleic acids. Each T cell bears a unique receptor called the T cell receptor (TCR) that is capable of recognizing a specific antigen-MHC complex. Through rearrangement of the gene segments containing the protein-coding segments of the TCR, a vast array, perhaps a virtually unlimited number of combinations, of different TCRs are generated (33). By a mechanism termed "allelic exclusion", each T cell bears a single unique TCR. The T cell repertoire is therefore a large number of T cells, each with a distinct TCR that recognizes a specific antigen-MHC complex. It is this vast array of T cells that allows immunological responses to the diversity of antigenic structures on invading micro-organisms, tumor cells, and allografts, thus preserving the integrity of the organism.

Most antigens are able to elicit a response in only a very tiny fraction of the T cell repertoire (34). For example, the initial response to protein antigens may involve as few as $\frac{1}{1000}$ to $\frac{1}{10,000}$ T lymphocytes (35). For this reason, diseases caused by T cell reactivity are mediated by only a small subset of the large repertoire of T cells (36). In particular, in those cases where it has been directly measured, such as in multiple sclerosis, the fraction of the T cell repertoire which mediates disease is quite small (36). The important feature of the T cell subset that participates in disease is that it involves T cells which specifically recognize an antigen that provokes the disease. In allergic conditions, the antigen causes the release of inflammatory response molecules. In autoimmune diseases, the antigen may be derived from a specific organ in the body and, when recognized by a subset of T cells, stimulates the T cells to attack that organ. A similar effect occurs during graft rejection. Antigenic proteins in the transplanted organ evoke a response in a subset of T cells that attacks the engrafted tissue. For unknown reasons, the fraction of T cells recognizing foreign or "allo" tissue is significantly higher than the number that will typically recognize a protein antigen. Nonetheless, the number of responding T cells is still a distinct minority (1–10%) of the overall T cell repertoire (37).

In a typical response to a specific antigen-MHC complex, the T cells undergo a cascade of gene activation events that results from stimulation of the TCR (38). These have been extensively characterized at the molecular level, and two such activation events are especially germane to the present therapy: production of the lymphokine IL-2, and expression of the cell surface proteins that constitute high-affinity receptors for IL-2. IL-2 is a 15,000 dalton protein that causes T cells bearing the appropriate high affinity receptor to divide (68). Non-activated T cells do not express high affinity IL-2 receptors (39). The production of IL-2 followed by its interaction with its receptor causes an autocrine mechanism that drives the T cells into the cell cycle (39). This leads to an initial expansion of T cells that are specifically reactive with the antigen. The present inventive discovery indicates that IL-2 also has the surprising effect of predisposing the expanded pool of either human or mouse T cells to apoptosis or programmed cell death if they are again stimulated or rechallenged through the TCR (30, 74). In the present work described supra, the degree of apoptosis achieved in either human or mouse T cells is correlated positively with both the level of IL-2 the cells experience during their initial expansion, the strength of the TCR stimulation upon rechallenge, and the timing of the rechallenge. The effects of IL-2 wear off 2–3 days after IL-2 is no longer present, hence rechallenge must occur within that period (94). The process of activation and apoptosis eventually depletes the antigen-reactive subset of the T cell repertoire. Apoptosis denotes a type of programmed cell death in which the T cell nucleus shrinks, the genetic material (DNA) progressively degrades, and the cell collapses (1, 40). Evidence would suggest that cells cannot recover from apoptosis, and that it results in irreversible killing (1, 40). T cells that do not undergo apoptosis but which have become activated will carry out their "effector" functions by causing cytolysis, or by secreting lymphokines that cause B cell responses or other immune effects (41). These "effector" functions are the cause of tissue damage in autoimmune and allergic diseases or graft rejection. A powerful approach to avoiding disease would therefore be to permanently eliminate by apoptosis only those T cells reactive with the disease-inciting antigens, while leaving the majority of the T cell repertoire intact.

By using IL-2 as an agent that predisposes T cells to death by TCR stimulation in appropriate cycle with immunization with the antigen(s) leading to autoimmune disease or graft rejection, the death of disease-causing T cells can be invoked. Specific methods are described for i) treatment of autoimmune or allergic diseases by identified protein antigen and IL-2, and ii) treatment of graft rejection by blood cell antigens and IL-2. Such methods, by logical extension, can be further developed for other diseases of man or animals that result from the effects of T cells activated by specific antigens. Because the vast majority of immune responses depend on T cell activation, whether cytotoxic responses or antibody production are involved, it is predicted that this form of therapy could be applied to a wide variety of autoimmune and allergic conditions (100, 106).

II. Method for IL-2/peptide-mediated apoptosis of T lymphocytes.

In several human autoimmune diseases, data have indicated that antigen-activated T cells play a key role in the production of disease. These include but are not limited to: 1) multiple sclerosis (42–47); 2) uveitis (48, 49)); 3) arthritis (50–52); 4) Type I (insulin-dependent) diabetes (53, 54); 5)

Hashimoto's and Grave's thyroiditis (55–57); and 6) autoimmune myocartiditis (58). The ethical limits on human experimentation have made it very difficult to prove that T reactivity is the sole inciting agent of these diseases. Nonetheless, a large body of experimental work on animal models—murine experimental allergic encephalitis as a model for multiple sclerosis (59, 60), BB diabetic rats for human diabetes (61, 62), murine collagen-induced arthritis for rheumatoid arthritis (63, 64), and S antigen disease in rats and guinea pigs for human autoimmune uveitis (65, 66), among others—suggests that T cells are the critical agent of these diseases. From recent work, the identity of disease-causing proteins or peptide antigens is emerging: i) multiple sclerosis: the peptide epitopes of myelin basic protein (MBP) residues 84–102 and 143–168 (45, 66, 67); ii) autoimmune uveitis: the human S antigen, which has been recently molecularly cloned (48, 69); iii) type II collagen in rheumatoid arthritis (70); and iv) thyroglobulin in thyroiditis (71). Similarly, a wide variety of proteins have been identified which stimulate the production of the allergic immunoglobulin, IgE. IgE is produced by β lymphocytes in a process that requires lymphokines produced by antigen-activated T cells known as "T cell help".

The basic concept of the present therapeutic approach is very simple. Disease-causing T cells are first challenged by immunization, which causes the activated T cells to express high affinity IL-2 receptors and to begin producing and secreting IL-2. When the cells are expressing high levels of IL-2 receptor, additional human IL-2 is infused to very efficiently drive all the activated cells into cycle. The cells under the influence of IL-2 are then caused to undergo apoptosis by re-immunization with antigenic peptide or protein. Further, if the antigen is capable of stimulating sufficient IL-2 production, it is not necessary to administer exogenous IL-2. In either case, the timing of rechallenge is important—it must occur within a short interval such as 2–3 days after the first stimulus when cells bear the IL-2 receptor and are responding to exogenous or endogenous IL-2.

Figure 4:
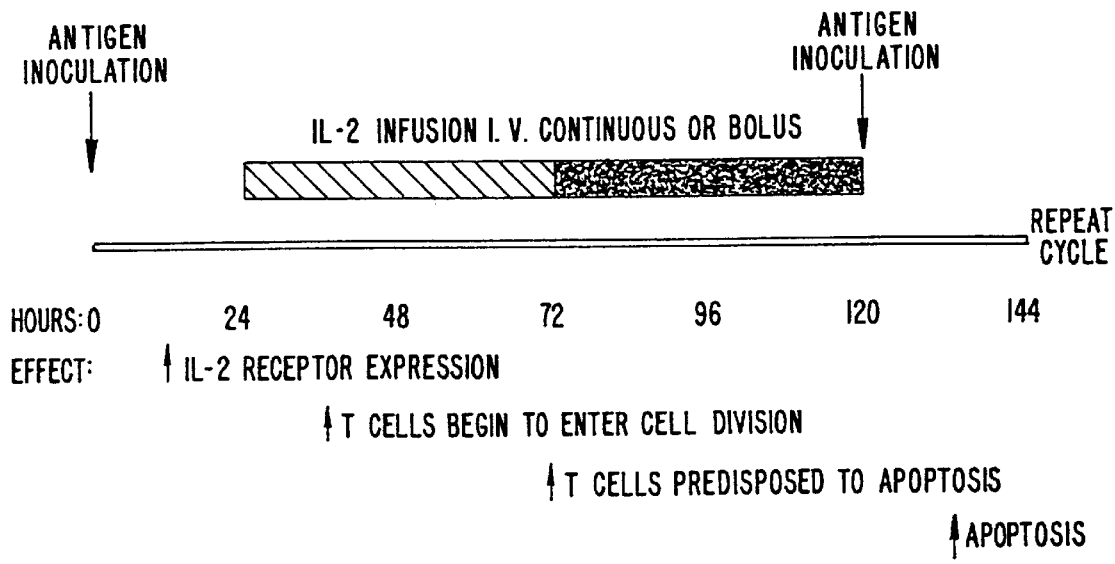
FIG. 4 summarizes the therapeutic protocol for the induction of apoptosis of the present invention.

Protocol:

As shown in FIG. 4, immunization with a specific peptide or protein is carried out on day one. In the case of multiple sclerosis, for example, either of two immunodominant peptides from myelin basic protein (MBP) believed to be encephalitogenic in man, MBP 84–102 (the preferred peptide), or MBP 143–168 (66–68), that have been coupled to tetanus toxoid, can be given in alum adjuvant IM, at a dose between about 10 to about 1000 μg. Previous experience using proteins or peptides has suggested that intramuscular (IM) administration is optimal (85–87, 89, 90). Newer data suggest that oral administration may also be effective (73).

As with any medicinal substance, or biologic, tests on any peptides and proteins used for the immunization would need to be routinely carried out over a range of doses to determine: 1) the pharmacokinetic behavior of these substances; 2) their immunogenicity; and 3) safety and identification of any untoward effects. This would constitute a Phase I clinical trial (84). Thus, the particular proteins or peptides employed in this protocol (for example, in multiple sclerosis, MBP 84–102, or MBP 143–168; in uveitis, the S Antigen; or in rheumatoid arthritis, type II collagen) would require individual routine optimization. Similar intervention could be used with preparations of allergy-inducing proteins. These could be derived from a variety of allergen protein extracts that are now used clinically, or could be generated by recombinant DNA technology for those such as hornet venom antigen 5, for which cDNA clones are available (103). Ample evidence from the development of vaccines suggests that either synthetic peptides or recombinant DNA-derived proteins are effective in eliciting an immune response in humans (85–90). These studies also provide guidance as to the range of doses effective for immunization.

Proteins:

1) Hepatitis B surface antigen, produced as a recombinant protein in yeast. Adults 2.5 to 20 μg; children 1.25 to 5 μg intramuscularly (IM). 90–96% of vaccines showed an immune response, with the best response at 10–20 μg (85). Further studies showed the efficacy of a 10 μg dose, with better results when given IM rather than subcutaneously (86). 20 μg doses in alum adjuvant given IM were found to be effective at preventing infection in clinical trials (87).

2) HIV gp 120, either natural or recombinant molecules. Doses in chimpanzees between 50–1000 μg elicit T cell responses (88).

Peptides:

1) Chorionic gonadotropin. Several studies have indicated successful immune responses against a human chorionic gonadotropin-β subunit peptide (residues 109–145) coupled to cholera or tetanus toxoid and given in doses from 50–1000 μg in alum adjuvant (89).

2) Malaria sporozoite antigen. Studies of a *Plasmodium falciparum* peptide (NANP)$_3$ coupled to tetanus toxoid showed an immune response to doses of 20–160 μg of peptide conjugate given IM, with the best response at 160 μg (90).

Figure 5:
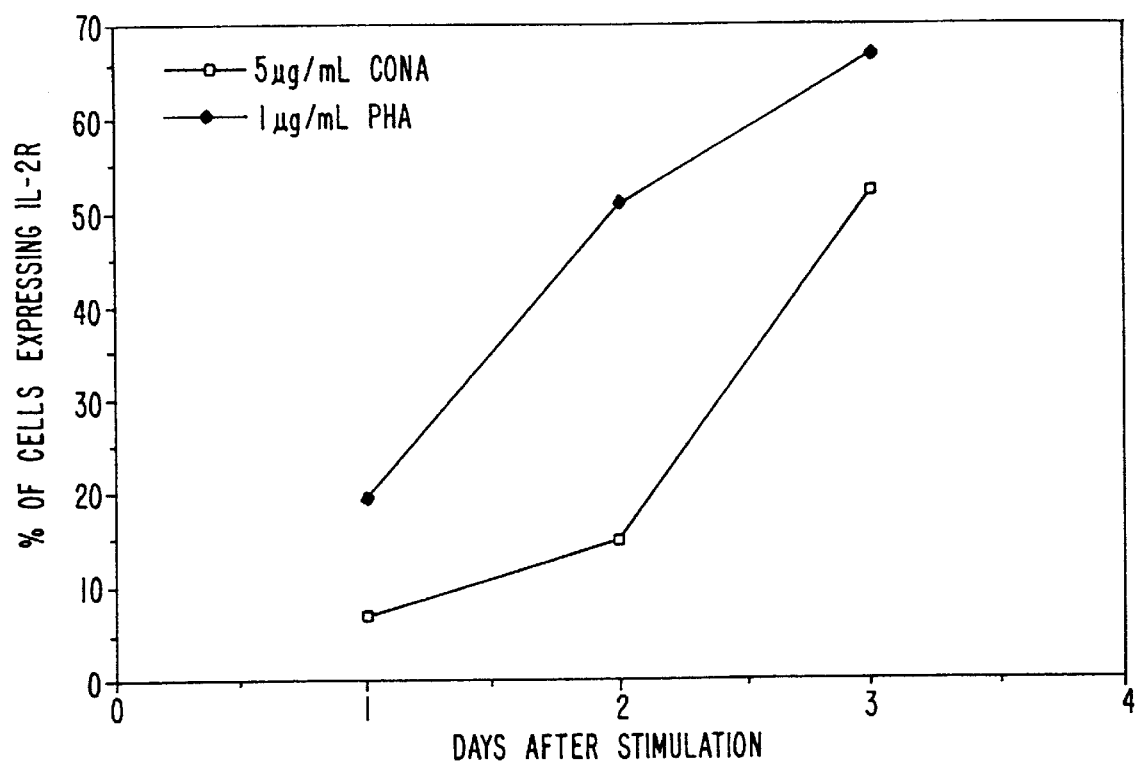
FIG. 5 shows the time course of expression of the IL-2 receptor on human peripheral blood T cells after stimulation with various antigens.

Immunization is then followed by a waiting period during which the antigen activates the subset of T cells bearing reactive TCRs, causing them to express IL-2 and IL-2 receptors. This process will only induce IL-2 receptors on cells that have been antigenically-stimulated (39). Based on studies of both human and mouse T cells in vitro, between about 12 to about 24 hours after antigen exposure are required to express significant numbers of IL-2 receptors, and as long as about 72 hours are required to express optimal numbers of IL-2 receptors on the majority of T cells (74; FIG. 5). Thus, the waiting period can be as short as about 12 hours or as long as about 72 hours, becoming increasingly optimal toward the upper end of this range.

FIG. 5: Human peripheral T lymphocytes were stimulated with either 5 μg/ml concanavalin A or 1 μg/ml phytohemagglutinin for various time periods. The cells were then harvested, washed and stained with FITC-labelled anti-IL-2Rα MAb specific for the human protein (anti-Tac). Flow cytometry was carried out on a Becton-Dickinson FACS-CAN cytometer and analyzed using the Lysis II software.

This is then followed by an infusion of high doses of IL-2. The administration of high-dose IL-2 to humans has been well-studied in cancer patients, and various doses have been evaluated (75–79). A number of ongoing protocols evaluating the medical uses of IL-2 presently exist (95). Data indicate that IL-2 should be given I.V., either as frequent bolus doses or as a continuous infusion (75–77). Doses that have been previously established range between about 300 to about 3000 units/kg/hour continuous infusion, or from $10^4$ to $10^6$ units/kg I.V. bolus (76). Units are defined by standards available from the Biological Response Modifiers Program at the National Institutes of Health, and are defined as the quantity of IL-2 that gave 50% maximal thymidine incorporation in the bioassay under standard conditions. Side effects of these doses included chills, fever, malaise, headache, nausea and vomiting, weight gain due to fluid retention, diarrhea, rash, and pruritis, which can all be treated with acetaminophen or indomethacin; no serious morbidity or mortality was observed. Despite the apparent short half-life of IL-2 in serum, at a dose of 3000 u/kg/hr, IL-2 was detected in patient serum at a level of 5–10 units/ml. These levels have been found to predispose on the order of 60–70% of the T cells to apoptosis, supra. IL-2 infusion can be continued for about 48 to about 72 hours, a time frame shown to ensure that IL-2 receptor bearing cells are stimulated into the cell cycle and pre-disposed to apoptosis (supra, and 74). A 48–72 hour treatment should avoid the serious complication of excessive fluid retention even at high doses of IL-2 (76). After IL-2 treatment, the patient can be immediately reimmunized with an equivalent dose of antigen. For example, for multiple sclerosis, treatment can be with about 10 to about 1000 μg of peptide 84–102 coupled to tetanus toxoid and given in alum adjuvant IM. It is likely that the preferred dose would be near the upper end of this range since greater TCR stimulation produces a greater level of apoptosis (94). IL-2 treatment would have stimulated the T cells bearing IL-2 receptors—predominantly the disease-causing T cells—and these cells would then be re-stimulated through their TCR. These cells will then undergo apoptosis (supra, 74). After an immunization period of about 12 to about 72 hours, the cycle would begin again with reinfusion of IL-2. As will be described below, increased efficacy would likely result from multiple cycles of therapy. The treatment endpoints would be: i) elimination of in vitro reactivity to the antigen, which can be easily measured where possible by various mixed lymphocyte or proliferation assays using peripheral blood lymphocytes; ii) amelioration of clinical symptoms; or iii) toxicity. The treatment endpoints for allergic diseases would be: i) improvement of clinical symptoms; ii) normalization of an allergic skin test; iii) reduction in serum IgE levels; and iv) where possible to measure, reduced T cell responses to the allergenic protein.

Several features of the present therapy require further explanation. First, it is expected that T cells besides those antigenically stimulated will express high affinity IL-2 receptors. Treatment with high doses of IL-2 causes expression of the high affinity IL-2 receptor in a small fraction of resting T lymphocytes (76). However, this should not diminish the specificity of the therapy because only those cells whose TCRs are stimulated by rechallenge with antigen will undergo apoptosis, as described supra. The effectiveness of the therapy could be variable depending on the nature of the antigen and the exact protocol employed. Extensive in vitro studies indicate that between 50–80% of the antigen-specific IL-2 stimulated T cells will undergo apoptosis when rechallenged by TCR stimulation (supra, 76). Second, the reduction in number of antigen-specific T cells determines the overall effectiveness of the therapy. Therefore, repeated cycles can substantially increase efficacy even if the level of killing in each cycle is only 50–70% (Table 3). As shown in the mouse studies, supra, the level of antigen-reactive T cells will decrease below the number of such cells prior to the first immunization with repetitive immunization. Furthermore, the expected toxicity of this protocol should be minor, and previous studies of the therapeutic use of IL-2 in humans indicates that all side effects dissipate promptly following the discontinuation of IL-2 (75, 76). The most serious side effect, fluid retention, should be minimized by the intermittent nature of IL-2 treatment (79). The 2–3 day rest period between doses would allow for diuresis of the fluid built up during IL-2 administration. Finally, the repeated administration of antigen will cause production of some endogenous IL-2, which will predispose some cells to apoptosis. While it is extremely unlikely that endogenous levels can reach the very high levels of IL-2 that can be administered pharmacologically, it is possible that empirically-determined decreases in the IL-2 dose could be achieved because of endogenous IL-2 effects. The level of killing is dependent on the total level of IL-2 to which the T cell is exposed, and this will reflect a combination of endogenous and exogenous sources (supra, 76).

With certain antigens, the pre-disposition of cells to apoptosis may be sufficiently induced by the endogenous production of IL-2. In these cases, appropriate immunization with antigen, in the absence of exogenously administered IL-2, could produce T cell apoptosis and a protective effect. Based on the studies of the timing of susceptibility to apoptosis disclosed supra, immunizations repeated at specific intervals would be crucial for effective therapy. To effect IL-2-mediated apoptosis, immunizations would have to be repeated at about 24 to about 120 hour intervals, preferably at about 24 to about 72 hour intervals, and would have to be repeated multiple times. T cell reactivity or cell-mediated immunity for the specific antigen could then be monitored by in vitro assays to determine that T cells had undergone apoptosis. Absent the knowledge provided by the discovery disclosed herein, previous attempts to decrease immune responsiveness by repetitive immunization have not been optimal. For example, donor transfusion protocols to ameliorate graft rejection involved 3 transfusions given at 2 week intervals (91, 92). Allergy shots, i.e., desensitization therapy, are typically given initially at 4–7 day intervals, after which intervals are progressively increased in length to 2 to 4 weeks (102). Based on the present novel understanding of T cell apoptosis, the most effective immunization protocol would involve repetitive administrations of antigen at about 24 to 72 hour intervals.

TABLE 3

Theoretical number of reactive cells after fractional killing using IL-2 and T cell receptor stimulation

| Cycle | Fractional Killing | Reactive Cells Remaining |
|---|---|---|
| Start | None | 100,000 |
| 1 | 70% | 30,000 |
| 2 | 70% | 9,000 |
| 3 | 70% | 2,700 |
| 4 | 70% | 810 |
| 5 | 70% | 243 |
| 6 | 70% | 73 |

Theoretical values are based on starting with 100,000 cells and a constant killing efficiency of 70%. A reduction of over 100-fold is seen in 4 cycles and over 1000-fold in 6 cycles. At a fractional killing of 50%, a reduction of nearly 100-fold would be seen in 6 cycles.

III. Method for transplantation antigen/IL-2-mediated apoptosis.

In medical procedures in which tissue is transferred between individuals who are genetically non-identical at their relevant histocompatibility antigen loci, herein referred to as allografting, and the tissue as an allograft, the major problem encountered is rejection of the donor allograft by the host. The term "host" refers to the individual who is the recipient of the allograft, and the term "donor" refers to the individual from whom the allograft is derived. Studies of the process of graft rejection have shown that it is due to the antigen-specific activation of T lymphocytes, especially those bearing CD8 surface molecules (80). More importantly, agents that block the ability of T cells to mount an immune response in humans effectively prevent or lessen graft rejection (81). Since CD8$^+$ T cells have been shown to be susceptible to apoptosis by IL-2, supra, this phenomenon can be used as a specific means to eliminate the reactive T cells, thereby avoiding graft rejection.

Protocol: Essentially the same protocol with respect to timing and IL-2 dose can be used for this therapy as was described supra for the therapy of autoimmune diseases. The major difference between this therapy and that described above is the source of antigen. Major histocompatibility complex (MHC) antigens are cell surface proteins that are tremendously polymorphic among individuals. Each individual's cells bear a genetically determined set, or haplotype, of such antigens which serve as an immunological "fingerprint" on each cell (82). This allows one's immune system, in particular those responses generated by T cells, to recognize one's own cells, and to attack only cells that do not bear the self "fingerprint" (83). There are two classes of MHC—class I antigens, found on all cells in the body; and class II antigens, found predominantly on monocytes, macrophages, B lymphocytes, dendritic cells, and activated T cells (82). It is the class I MHC antigens that are recognized by $CD8^+$ T cells that are the predominant influence in allograft rejection (80, 83). Because of this complexity of MHC antigens, the simplest source is cells from the allograft donor. It has been empirically observed that transfusion of a graft recipient with donor blood suppresses graft rejection, although the mechanism of this effect is unknown, and the clinical effectiveness in many cases is modest (92). These protocols provide evidence that three transfusions of 200 ml of whole blood or packed cell equivalent from the donor is easily tolerated by the recipient with minimal side effects (91). There is evidence that the donor-transfusion in some cases elicited sensitizing antibody responses in the allograft host, and these patients were not given allografts (91). These studies possibly represent an empirical observation that pre-exposure to donor antigen suppresses the T cell response, although this is controversial (93). The present method includes administration of blood as a source of MHC antigens in doses of about 50 to about 200 ml to patients in cycle with IL-2, as indicated in FIG. 4. In the case of kidney transplants, the amount of blood could be determined by the fluid tolerance of end-stage renal disease patients. The blood can be given as either whole blood, packed cells, or washed packed cell transfusions (92). The success of treatment can be assessed by: i) a decreased requirement for general immunosuppressive medications; ii) graft survival; and iii) adequate function of the allograft. For example, the function of a transplanted kidney can be established by determining serum levels of creatinine and blood urea nitrogen (104). This can be followed by IL-2 infusion and rechallenge with blood cells as antigen as shown in FIG. 4.

IV. Summary.

The conceptual advance provided by the inventive discovery that underlies the present methods is that T cell immunity works as a balance between the production and destruction of antigen-specific T lymphocytes. Previously, investigators have focused on the use of lymphokine growth factors such as IL-2 to increase the proliferation and responsiveness of T lymphocytes (68). It is now proposed that the opposing T cell mechanisms be used therapeutically. The discovery that IL-2 predisposes T cells to death is contrary to the previously understood properties of IL-2, and provides a radically new approach to the treatment of diseases caused by T cell reactivity. By providing physicians and medical researchers with the basis of the present inventive discovery, the processes of immune autoregulation leading to T cell destruction can be exploited in combatting disease.

It has been previously known for some time that prior activation and IL-2 production were capable of diminishing immune responsiveness both in vivo and in vitro (1–4, 95–97). The mechanism for these effects was not understood. Absent the knowledge that IL-2 predisposes T lymphocytes to antigen-dependent apoptosis, it was not possible to manipulate this phenomenon for medical or therapeutic purposes. Recent results demonstrate that human T lymphocytes are quite susceptible to apoptosis following IL-2 exposure (74). It is now possible to rigorously study the kinetics and dose requirements of IL-2 in the predisposition phase, and antigen in the apoptosis phase, to routinely optimize the treatment cycle for a given disease following the guidance provided herein.

That this process depends on the discovery of a novel property of IL-2 is particularly auspicious. IL-2 is perhaps the best studied lymphokine (68). It is well-understood genetically, its cDNA and gene have been molecularly cloned, and its mRNA expression has been thoroughly studied (68). IL-2 is already available pharmaceutically in a form for use in humans (79). Previous studies in human cancer victims, detailed above, have given clear insights into how IL-2 affects human physiology at different doses (79). All of these features significantly enhance the feasibility of its novel use to cause auto-destruction of disease-causing T lymphocytes for the treatment of a wide variety of diseases in humans and other mammals.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

LITERATURE CITED

1. Kawabe, Y. & Ochi, A. Nature 349, 245–248 (1991).
2. Russell, J. H., White, C. L., Loh, D. Y. & Meleedy-Rey, P. Proc. Natl. Acad. Sci. 88, 2151–2155 (1991).
3. Liu, Y. & Janeway, C. A. Jr. J. Exp. Med. 172, 1735–1739 (1990).
4. Webb, S., Morris, C. & Sprent, J. Cell 63, 1249–1256 (1990).
5. Smith, C. A., Williams, G. T., Kingston, R., Jenkinson, E. R. & Owen, J. T. Nature 337, 181–184 (1989).
6. MacDonald, H. R. & Lees, R. K. Nature 343, 642–644 (1990).
7. Murphy, K. M., Heimberger, A. B. & Loh, D. Y. Science 250, 1720–1723 (1990).
8. Jones, L. A., Chin, L. T., Longo, D. L. & Kruisbeek, A. M. Science 250, 1726–1729 (1990).
9. Rocha, B. & von Boehmer, H. Science 251, 1225–1228 (1991).
10. Hecht, T. T., Longo, D. L. & Matis, L. A. J. Immunol. 131, 1049 (1983).
11. Ashwell, J. D., Robb, R. J. & Malek, T. R. J. Immunol. 137, 2572–2578 (1986).
12. Nau, G. J., Moldwin, R. L., Lancki, D. W., Kim, D-K., & Fitch, F. W. J. Immunol. 139, 114–122 (1987).
13. Williams, M. E., Lichtman, A. H. & Abbas, A. K. J. Immunol. 144, 1208–1214 (1990).
14. Weaver, C. T., Hawrylowicz, C. M. & Unanue, E. R. Proc. Natl. Acad. Sci. 85, 8181–8185 (1988).
15. Mueller, D. L., Jenkins, M. K. & Schwartz, R. H. J. Immunol. 142, 2617–2628 (1989).
16. Leo, O., Foo, M., Sachs, D. H., Samelson, L. E. & Bluestone, J. A. Proc. Natl. Acad. Sci. USA 84, 1374–1378 (1987).

17. Staerz, U. D., Rammensee, H- G., Benedetto, J. D. & Bevan, M. J. *J. Immunol.* 134, 3994–4000 (1985).
18. Kanagawa, D., *J. Exp. Med.* 170, 1513–1519 (1989).
19. White, J., Herman, A., Pullen, A. M., Kubo, R., Kappler, J. W. & Marrack, P. *Cell* 56, 27–35 (1989).
20. Haskins, K., Hannum, C., White, J., Roehm, N., Kubo, R., Kappler, J. & Marrack, P., *J. Exp. Med.* 160, 452–471 (1984).
21. Malek T. R., Ortega R., G., Jakway, J. P., Chan, C. & Shevach, E. M. *J. Immunol.* 133, 1976–9182 (1984).
22. Tentori, L., Longo, D. L., Zuniga-Pflucker, J. C., Wing, C. & Kruisbeek, A. M. *J. Exp. Med.* 168, 1741–1747 (1988).
23. Ohara, J. & Paul, W. E. *Nature* 315, 333–336 (1985).
24. Finkelman, F. D., Katona, I. M., Urban, J. F. Jr., Snapper, C. M., Ohara, J. & Paul, W. E. *Proc. Natl. Acad. Sci.* 83, 9675–9678 (1986).
25. Monod, J. & Jacob, F. *Cold Spring Harbor Symposium* 26, 389–401 (1961).
26. Marrack, P., Blackman, M., Kushner, E. & Kappler, J. *J. Exp. Med.* 171, 445–464 (1990).
27. Penit, C. & Vasseur, F. J. Immunol. 140, 3315–3323 (1988).
28. Janssen, O., Wesselborg, S., Heckl-Ostreicher, B., Pechhold, K., Bender, A., Schondelmaier, S., Modenhauer, G. & Kabelitz, D. *J. Immunol.* 146, 35–39 (1991).
29. Crispe, I. N., Bevan M. J. & Staerz, U. D. *Nature* 317, 627–629 (1985).
30. Lenardo, M. J., Interleukin-2 programs mouse $\alpha\beta$ T lymphocytes for apoptosis, *Nature* (1991). Submitted.
31. Katz, P. and A. S. Fauci, Immunosuppressives and immunoadjuvants, *Immunological Diseases*, M. Somter et al., eds. (Boston: Little, Brown and Company), pp. 675–698 (1989).
32. Weiss, A., T lymphocyte activation, *Fundamental Immunology*, Second Ed., W. E. Paul, ed. (New York: Raven Press), pp. 359–384 (1989).
33. Hedrick, S. M., T lymphocyte receptors, *Fundamental Immunology*, Second Ed., W. E. Paul, ed. (New York: Raven Press), pp. 291–358 (1989).
34. Fink, P. J., M. J. Blair, L. A. Matis and S. M. Hedrick, Molecular analysis of the influences of positive selection, tolerance induction, and antigen presentation on the T cell repertoire. *J. Exp. Med.,* 172:139 (1990).
35. Tse, H. Y., R. H. Schwartz and W. E. Paul, Cell—cell interactions in the T cell proliferative response, *J. Immunol.,* 125:491–500 (1980).
36. Oksenberg, J. R., S. Stuart, A. B. Begovich, R. B. Bell, H. A. Erlich, L. Steinman and C. C. A. Bernard, Limited heterogeneity of rearranged T-cell receptor V$\alpha$-transcripts in brains of multiple sclerosis patients, *Nature* 345:344 (1990).
37. Lindahl, K. F. and D. B. Wilson, Histocompatibility antigen-activated cytotoxic T lymphocytes, *J. Exp. Med.* 145:508–522 (1977).
38. Crabtree, J., Contingent genetic regulatory events in T lymphocyte activation, *Science* 243:355–361 (1989).
39. Waldman, T., The multi-subunit interleukin-2 receptor, *Ann. Rev. Biochem.* 58:875–911 (1989).
40. Smith, C. A., G. T. Williams, R. Kingston, E. J. Jenkinson and J. J. T. Owen, Antibodies to CD3/T-cell receptor complex induce death by apoptosis in immature T cells in thymic cultures, *Nature* 337:181–184 (1989).
41. Paul, W. E., The immune system: an introduction. *Fundamental Immunology*, Second Ed., W. E. Paul, ed. (New York: Raven Press) pp. 3–38 (1989).
42. Johnson, D, D. A. Hafler, R. J. Fallis, M. B. Lees, R. O. Brady, R. H. Quarles and H. L. Weiner, Cell-mediated immunity to myelin-associated glycoprotein, proteolipid protein, and myelin basic protein in multiple sclerosis, *J. Neuroimmunology* 13:99–108 (1986).
43. Martin, R., M. D. Howell, D. Jaraquemada, M. Flerlage, J. Richert, S. Brostoff, E. O. Long, D. E. McFarlin and H. F. McFarland, A myelin basic protein peptide is recognized by cytotoxic T cells in the context of four HLA-DR types associated with multiple sclerosis, *J. Exp. Med.,* 173:19–24 (1991).
44. Pette, M., K. Fujita, D. Wilkinson, D. M. Altmann, J. Trowsdale, G. Giegerich, A. Hinkkanen, J. T. Epplen, L. Kappos and H. Wekerle, Myelin autoreactivity in multiple sclerosis: recognition of myelin basic protein in the context of HLA-DR2 products by T lymphocytes of multiple-sclerosis patients and healthy donors. *Proc. Natl. Acad. Sci. USA* 87:7968–7972 (1990).
45. Jaraquemada, D., R. Martin, S. Rosen-Bronson, M. Flerlage, H. F. McFarland and E. O. Long, HLA-DR2a is the dominant restriction molecule for the cytotoxic T cell response to myelin basic protein in DR2Dw2 individuals, *J. Immunol.* 145:2880–2885 (1990).
46. Martin, R., D. Jaraquemada, M. Flerlage, J. Richert, J. Whitaker, E. O. Long, D. E. McFarlin and H. F. McFarland, Fine specificity and HLA restriction of myelin basic protein-specific cytotoxic T cell lines from multiple sclerosis patients and healthy individuals, *J. Immunol.* 145:540–548 (1990).
47. Brinkman, C. J. J., W. M. Nillesen, O. R. Hommes, K. J. B. Lamers, B. E. depauw, and P. Delmotte, Cell-mediated immunity in multiple sclerosis as determined by sensitivity of different lymphocyte populations to various brain tissue antigens, *Ann. Neurology* 11:450–455 (1981).
48. Hirose, S., L. A. Donoso, T. Shinohara, A. G. Palestine, R. B. Nussenblatt and I. Gery, Lymphocyte responses to peptide M and retinal S antigen in uveitis patients, *Jpn. J. Ophthalmol.* 34:298–305 (1990).
49. de Smet, M. D., J. H. Yamamoto, M. Mochizuki, I. Gery, V. K. Singh, T. Shinohara, B. Wiggert, C. J. Chader and R. B. Nussenblatt, Cellular immune responses of patients with uveitis to retinal antigens and their fragments, *Am. J. Ophthalmol.* 110:135–142 (1990).
50. Hawrylko, E., A. Spertus, C. A. Mele, N. Oster and M. Frieri, Increased interleukin-2 production in response to human Type I collagen stimulation in systemic sclerosis patients, *Arthritis Rheum.,* 34:580–587 (1991).
51. Abdel-Nour, A. N., C. J. Elson and P. A. Dieppe, Proliferative responses of T-cell lines grown from joint fluids of patients with rheumatoid arthritis and other arthritides, *Immunol. Lett.* 12:329–33 (1986).
52. Paliard, X., S. G. West, J. A. Lafferty, J. R. Elements, J. W. Kappler, P. Marrack and B. L. Kotzin, Evidence for the effects of a superantigen in rheumatoid arthritis, *Science* 253:325–329 (1991).
53. Bottazzo, G. F., B. M. Dean, J. M. McNally, E. H. MacKay, P. G. F. Swift and D. R. Gamble, In situ characterization of autoimmune phenomena and expression of HLA molecules in the pancreas in diabetic insulitis, *New Engl. J. Med.* 313:353–360 (1985).
54. Lundkin, K. E., G. Gaudernack, E. Qvigstad, L. M. Sollid and E. Thorsby, T lymphocyte clones recognizing an HLA-DQw3.2-associated epitope involving residue 57 on the DQ beta chain, *Human Immunol.,* 22:235:46 (1988).
55. Davies, T., A. Martin, E. S. Concepcion, P. Graves, L. Cohen and A. Ben-nun, Evidence of limited variability of 55. antigen receptors on intrathyroidal T cells in autoimmune thyroid disease, *New Eng. J. Med.* 325:238–244 (1991).
56. Volpe, R., Immunoregulation in autoimmune thyroid disease, *New Eng. J. Med.* 316:44–46 (1987).
57. Londei, M., G. F. Bottazzo and M. Feldman, Human T-cell clones from autoimmune thyroid glands: specific recognition of autologous thyroid cells, *Science* 228:85–89 (1985).
58. Dale, J. B. and E. H. Beachey, Sequence of myosin-crossreactive epitopes of streptococcal M. protein, *J. Exp. Med.*, 164:1785–1790 (1986).
59. Sobel, R. A., V. K. Tuohy and M. B. Lees, Parental MHC molecule haplotpe expression in $(SJL/J \times SWR)F_1$ mice with acute experimental allergic encephalomyelitis induced with two different synthetic peptides of myeline proteolipid protein, *J. Immunol.* 146:543–549 (1991).
60. Wraith, D. C., D. E. Smilek, D. J. Mitchell, L. Steinman and H. O. McDevitt, Antigen recognition in autoimmune encephalomyelitis and the potential for peptide-mediated immunotherapy, *Cell* 59:247–255 (1989).
61. Woda, B. A., E. S. Handler, D. L. Greiner, C. Reynolds, J. P. Mordes and A. A. Rossini, T-lymphocyte requirement for diabetes in RT6-depleted diabetes-resistant BB rats, *Diabetes* 40:423–8 (1991).
62. Metroz-Dayer, M. D., A. Mouland, C. Budeau, D. Duhmel and P. Poussier, Adoptive transfer of diabetes in BB rats induced by CD4 T lymphocytes, *Diabetes* 39:928–32 (1990).
63. Seki, N., Y. Sudo, A. Yamane, S. Sugihara, Y. Takai, K. Ishihara, S. Ono, T. Hamaoka, H. Senoh and H. Fujiwara, Type II collagen-induced murine arthritis. IL Genetic control of arthritis induction is expressed on L3T4+ T cells required for humoral as well as cell-mediated immune responses to type II collagen, *Reg. Immunol.*, 2:203–212 (1989).
64. Chiocchia, G., M. C. Boissier, M. C. Ronziere, D. Herbage and C. Fournier, T cell regulation of collagen-induced arthritis in mice. I. Isolation of type II collagen-reactive T cell hybridomas with specific cytotoxic function, *J. Immunol.*, 145:519–25 (1990).
65. Caspi, R. R., F. G. Rfoberge, C. G. Mcallister, M. ElSaied, T. Kuwabara, I. Gery, E. Hanna and R. B. Nussenblatt, T cell lines mediating experimental autoimmune uveoretinitis (EAU) in the rat, *J. Immunol.*, 136:9928–933 (1986).
66. Merryman, C. F., L. Donoso, X. M. Zhang, E. Heber-Katz and D. S. Gregerson, Characterization of a new potent immunopathogenic epitope in S-antigen that elicits T cells expressing Vβ8 and Vα2-like genes, *J. Immunol.* 146:75–80 (1991).
67. Ota, K., M. Matsui, E. L. Milford, G. A. Mackin, H. L. Weiner and D. A. Halfer, T-cell recognition of an immuno-dominant myelin basic protein epitope in multiple sclerosis, *Nature* 346:183–187 (1990).
68. Pette, M., K. Fujita, D. Wilkinson, D. M. Altmann, J. Trowsdale, G. Giegerich, A. Hinkkanen, J. T. Epplen, L. Kappas and H. Wekerle, Myelin autoreactivity in multiple sclerosis: recognition of myelin basic protein in the context of HLA-DR2 products by T lymphocytes of multiple-sclerosis patients and healthy donors, *Proc. Natl. Acad. Sci. USA* 87:7968–72 (1990).
69. Shinohara, T. V. K. Singh, M. Tsuda, K. Yamaki, T. Abe and S. Suzuki, S-Antigen: from gene to autoimmune uveitis, *Exptl. Eye Res.* 50:751–757 (1990).
70. Klimink, P. S., R. B. Claque, D. M. Grennan, P. A. Dyer, I. Smeaton and R. Harris, Autoimmunity to native type II collagen—a distinct subset of rheumatoid arthritis, *J. Rheum.*, 12:865–70 (1985).
71. Canonica, G. W., M. E. Cosulich, R. Croci, S. Ferrini, M. Bognasco, W. Dirienzo, D. Ferrini, A. Bargellesi and G. Giordano, TITLE, *Clinical Immunol. Immunopathol.* 32:132–41 (1984).
72. Annual Report of Intramural Activities, National Institutes of Allergy and Infectious Diseases, U.S. Department of Health and Human Services (1990).
73. Marx, J., Testing of autoimmune therapy begins, *Science* 252:27–28 (1991).
74. Mermelstein, A. and M. Lenardo, IL-2 predisposes human peripheral blood lymphocytes to apoptosis. Manuscript in preparation. (1991).
75. Lotze, M. T., L. W. Frana, S. O. Sharrow, R. J. Robb and S. A. Rosenberg, In vivo administration of purified human interleukin 2. I. Half-life and immunologic effects of the Jurkat cell line-derived interleukin 2. *J. Immunol.* 134:157–166 (1985).
76. Lotze, J. T., Y. L. Malory, S. E. Ettinghausen, A. A. Rayner, S. O. Sharrow, C. A. Y. Seipp, M. C. Custer and S. A. Rosenberg, In vivo administration of purified human interleukin 2. II. Half-life, immunologic effects, and expansion of peripheral lymphoid cells in vivo with recombinant IL 2. *J. Immunol.* 135:2865–2875 (1985).
77. Donohue, J. H. and S. A. Rosenberg, The fate of interleukin-2 after in vivo administration, *J. Immunol.* 130:2203–2208 (1983).
78. Belldegrun, A., M. M. Muul and S. A Rosenberg, Interleukin 2 expanded tumor-infiltrating lymphocytes in human renal cell cancer: isolation, characterization, and antitumor activity, *Cancer Research* 48:206–214 (1988).
79. Rosenberg, S. A., M. T. Lotze, L. M. Muul, S. Leitman, A. E. Chang, S. E. Ettinghausen, Y. L. Malory, J. M. Skibber, E. Shiloni, J. T. Vetto, C. A. Seipp, C. Simpson and C. M. Reichert, Observations on the systemic administration of autologous lymphokine-activated killer cells and recombinant interleukin-2 to patients with metastatic cancer, *New Eng. J. Med.* 313:1485–1492 (1985).
80. Auchincloss, H. and D. H. Sachs, Transplantation and graft rejection, *Fundamental Immunology*, Second Ed., W. E. Paul, ed. (New York: Raven Press) pp. 889–922 (1989).
81. Cosimi, A. B., R. C. Burton, R. B. Colvin, G. Goldstein, J. T. Herrin and P. S. Russell, Treatment of acute renal allograft rejection with OKT3 monoclonal antibody, *Transplantation*, 32:535–539 (1981).
82. Robinson, M. A. and T. J. Kindt, Major histocompatibility antigens and genes, *Fundamental Immunology*, Second Ed., W. E. Paul, ed. (New York: Raven Press) pp. 489–540 (1989).
83. Carbone, F. J. and M. J. Bevan, Major histocompatibility complex control of T cell recognition, *Fundamental Immunology*, Second Ed., W. E. Paul, ed. (New York: Raven Press) pp. 541–5701 (1989).
84. Owen, J. A. Jr., Managing and conducting Phase I and Phase II clinical trials, *Drug Develoment*, Second Ed., C. E. Hamner, ed. (Boca Raton: CRC Press) pp. 159–174 (1989).
85. Zajoc, B. A., D. J. West, W. J. McAleer and E. M. Scolnick, Overview of clinical studies with Hepatitis B vaccine made by recombinant DNA, *J. Infect.* 13:(Suppl A)39–45 (1986).
86. Yamamoto, S., T. Kuroki, K. Kurai and S. Iino, Comparison of results for phase I studies with recombinant and plasma-derived hepatitis B vaccines, and controlled study comparing intramuscular and subcutneous injections of recombinant hepatitis B vaccine, *J. Infect.* 13:(Suppl A) 53–60 (1986).
87. Francis, D. P. et al., The prevention of Hepatitis B with vaccine, *Ann. Int. Med.* 97:362–366 (1982).

88. Putney et al., Features of HIV envelope and development of a subunit vaccine, *AIDS Vaccine Research and Clinical Trials,* S. Putney and B. Bolognesi, eds. (New York: Dekker) pp. 3–62 (1990).
89. Steven, V. C. and W. R. Jones, Vacines to prevent pregnancy, *New Generation Vaccines,* G. C. Woodrow and M. M. Levine, eds. (New York: Dekker) pp. 879–900 (1990).
90. Herrington et al., Safety and immunogenicity in man of a synthetic peptide malaria vaccine against *Plasmodium Falciparium* sporozoites, *Nature,* 328:257–259 (1987).
91. Salvatierra, O. et al., Deliberate donor-specific blood transfusions prior to living-related renal transplantion, *Ann. Surg.* 192:543–551 (1980).
92. Opelz, G., M. R. Mickey and P. I. Terasaki, Blood transfusions and kidney transplants: remaining controversies, *Transpl. Proc.* 13:136–141 (1981).
93. Ruiz et al., Evidence that pre-transplant donor blood transfusion prevents rat renal allograft dysfunction but not the in situ autoimmune or morphologic manifestations of rejection, *Transplantation* 45:1–7 (1988).
94. Wallenhorst, M. and M. Lenardo, Manuscript in preparation.
95. Rellahan, B. L., L. A. Jones, A. M. Kruisbeek, A. M. Fry and L. A Matis, In vivo induction of anergy in peripheral Vβ8+T cells by Staphylococcal enterotoxin B, *J. Exp. Med.* 172:1091–1100 (1990).
96. Wilde, D. B. and F. W. Fitch, Antigen-reactive cloned helper T cells, I. Unresponsiveness to antigenic restimulation develops after stimulation of cloned helper T cells, *J. Immunol.* 132:1632–1638 (1984).
97. Otten, G., D. B. Wilde, M. B. Prystowsky, J. S. Olshan, H. Rabin, L. E. Henderson and F. W. Fitch, Cloned helper T lymphocytes exposed to interleukin 2 become unresponsive to antigen and concanavalin A but not to calcium ionophore and phorbol ester, *Eur. J. Immunol.* 16:217–225 (1986).
98. Schwartz, R. H., A cell culture model for T lymphocyte clonal anergy, *Science,* 248:1349–1356 (1990).
99. Morahan, G., Allison, J. and Miller, J.F.A.P., Tolerance of Class I histocompatibility antigens expressed extrathymically, *Nature,* 339:622–624 (1989).
100. Marsh, D. G. and Norman, P. S., Antigens that cause atopic diseases, Immunological Diseases, Fourth Edit., M. Samter et al, Eds. Vol. II, pp. 981–1002.
101. Toda, T., Regulation of reagin formation. *Prog. Allergy,* 19:122 (1975).
102. Grammer, L. C., Principles of immunologic management of allergic diseases due to extrinsic antigens, *Allergic Diseases, Diagnosis and Management,* Third Edit., R. Patterson, Ed., pp. 358–373.
103. Fang, K. S. Y., Vitale, M., Fehlner, P. and King, T. P., cDNA cloning and primary structure of a white-face hornet venom allergen, antigen 5, *Proc. Natl. Acad. Sci. USA,* 85:895–899 (1988).
104. Simmons, R. L. et al, Transplantation, *Principles of Surgery,* Fifth Edit., S. I. Schwartz, G. T. Shires, and F. C. Spencer, Eds., pp. 387–458.
105. Elsayed, S., Titlestead, K., Apold, J. et al. A synthetic hexapeptide derived from allergen M imposing allergenic and antigenic reactivity. *Scand. J. Immunol.,* 12:171 (1980).
106. Middleton, E. et al, Eds., *Allergy: Principles and Practice,* Third edition, (St. Louis: C. V. Mosby) (1988).
107. *Molec. Biol. Med.* 7:333–339.
108. El-Malik et al.,*Transplantation,* 38:213–216 (1984).
109. M. Wayne Flye, *Principles of Organ Transplantation,* (Philadelphia: W. B. Saunders) (1989).

What is claimed:

1. A method for inhibiting a T cell immune response associated with an autoimmune disease in a human subject, the method comprising repetitively administering to the patient an antigen specifically recognized by T cells, wherein the antigen is administered parenterally to cause the T cells that specifically recognize the antigen to express interleukin-2 (IL-2) or IL-2 receptors, such that the T cell immune response to the antigen is inhibited.

2. The method of claim 1, wherein the autoimmune disease is multiple sclerosis.

3. The method of claim 2, wherein the antigen is myelin basic protein.

4. The method of claim 1, wherein the autoimmune disease is autoimmune uveitis.

5. The method of claim 1, wherein the antigen is administered a about 24 to about 72 hour intervals.

6. The method of claim 1, wherein the antigen is a peptide.

7. The method of claim 6, wherein the peptide is administered at a dose between about 10 to about 1000 μg.

8. The method of claim 1, further comprising administering interleukin-2.

9. The method of claim 8, wherein the interleukin-2 is administered about 12 to about 72 hours after the antigen is administered.

10. The method of claim 8, wherein the interleukin-2 is administered parenterally.

11. A method for eliminating a subpopulation of T cells associated with an autoimmune disease in a sample, the method comprising contacting the sample with interleukin-2, followed by stimulation of the T cells.

12. The method of claim 11, wherein the step of stimulating the T cells is carried out by contacting the sample with an antigen recognized by the T cells.

13. The method of claim 11, wherein the autoimmune disease is multiple sclerosis.

14. The method of claim 1, wherein the antigen is administered at 2 to 3 day intervals.

* * * * *